US008657756B2

(12) United States Patent
Stahmann et al.

(10) Patent No.: US 8,657,756 B2
(45) Date of Patent: *Feb. 25, 2014

(54) IMPLANTABLE DEVICE EMPLOYING MOVEMENT SENSING FOR DETECTING SLEEP-RELATED DISORDERS

(75) Inventors: Jeffrey E. Stahmann, Ramsey, MN (US); Jesse W. Hartley, White Bear Lake, MN (US); Kent Lee, Shoreview, MN (US); Quan Ni, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 349 days.

This patent is subject to a terminal disclaimer.

(21) Appl. No.: 13/027,445

(22) Filed: Feb. 15, 2011

(65) Prior Publication Data

US 2011/0137197 A1    Jun. 9, 2011

Related U.S. Application Data

(62) Division of application No. 10/939,834, filed on Sep. 13, 2004, now Pat. No. 7,887,493.

(60) Provisional application No. 60/504,332, filed on Sep. 18, 2003.

(51) Int. Cl.
*A61B 5/08* (2006.01)
*A61B 5/04* (2006.01)
*A61B 5/05* (2006.01)

(52) U.S. Cl.
USPC ............................. 600/529; 600/546; 600/549

(58) Field of Classification Search
USPC ........................................ 600/529–543, 546
See application file for complete search history.

(56) References Cited

U.S. PATENT DOCUMENTS

| 3,650,277 A | 3/1972 | Sjostrand et al. |
| 4,091,818 A | 5/1978 | Brownlee et al. |
| 4,312,355 A | 1/1982 | Funke |

(Continued)

FOREIGN PATENT DOCUMENTS

| EP | 0547734 | 6/1993 |
| EP | 0750920 | 1/1997 |

(Continued)

OTHER PUBLICATIONS

Aug. 13, 2012, File History for U.S. Appl. No. 13/215,592.

(Continued)

*Primary Examiner* — Michael Kahelin
*Assistant Examiner* — Karen Toth
(74) *Attorney, Agent, or Firm* — Seager, Tufte & Wickhem LLC

(57) ABSTRACT

Methods and systems for evaluating a pathological condition include acquiring movement information, such as electromyogram (EMG) information, and sleep disordered breathing (SDB) information, and detecting the presence of a pathological condition using both movement and SDB information. Methods may involve sensing physiological signals including at least muscle movement signals. Sleep-related disorders are detected using the sensed physiological signals, the sleep-related disorders including at least an involuntary muscle movement disorder and sleep-disordered breathing. Methods and systems also provide for detecting and treating a sleep-related disorder using movement and SDB information. Cardiac, respiratory, nerve stimulation, drug, or a combination of such therapies may be delivered to treat a detected or diagnosed pathological condition.

20 Claims, 16 Drawing Sheets

(56) References Cited

U.S. PATENT DOCUMENTS

| | | |
|---|---|---|
| 4,312,734 A | 1/1982 | Nichols |
| 4,390,405 A | 6/1983 | Hahn et al. |
| 4,414,982 A | 11/1983 | Durkan |
| 4,648,407 A | 3/1987 | Sackner |
| 4,702,253 A | 10/1987 | Nappholz et al. |
| 4,721,110 A | 1/1988 | Lampadius |
| 4,777,962 A | 10/1988 | Watson et al. |
| 4,784,162 A | 11/1988 | Ricks et al. |
| 4,791,931 A | 12/1988 | Slate |
| 4,802,485 A | 2/1989 | Bowers et al. |
| 4,807,629 A | 2/1989 | Baudino et al. |
| 4,813,427 A | 3/1989 | Schlaefke et al. |
| 4,827,943 A | 5/1989 | Bornn et al. |
| 4,830,008 A | 5/1989 | Meer |
| 4,836,219 A | 6/1989 | Hobson et al. |
| 4,856,524 A | 8/1989 | Baker, Jr. |
| 4,860,766 A | 8/1989 | Sackner |
| 4,875,477 A | 10/1989 | Waschke et al. |
| 4,886,064 A | 12/1989 | Strandberg |
| 4,953,551 A | 9/1990 | Mehra et al. |
| 4,958,632 A | 9/1990 | Duggan |
| 4,961,423 A | 10/1990 | Canducci |
| 4,972,842 A | 11/1990 | Korten et al. |
| 4,982,738 A | 1/1991 | Griebel |
| 5,003,975 A | 4/1991 | Hafelfinger et al. |
| 5,010,888 A | 4/1991 | Jadvar et al. |
| 5,024,222 A | 6/1991 | Thacker |
| 5,047,930 A | 9/1991 | Martens et al. |
| 5,063,927 A | 11/1991 | Webb et al. |
| 5,074,301 A | 12/1991 | Gill |
| 5,101,831 A | 4/1992 | Koyama et al. |
| 5,111,815 A | 5/1992 | Mower |
| 5,123,425 A | 6/1992 | Shannon, Jr. et al. |
| 5,133,353 A | 7/1992 | Hauser |
| 5,146,918 A | 9/1992 | Kallok et al. |
| 5,156,157 A | 10/1992 | Valenta, Jr. et al. |
| 5,158,089 A | 10/1992 | Swezey et al. |
| 5,170,784 A | 12/1992 | Ramon et al. |
| 5,174,287 A | 12/1992 | Kallok et al. |
| 5,179,945 A | 1/1993 | Van Hofwegen et al. |
| 5,183,038 A | 2/1993 | Hoffman et al. |
| 5,188,106 A | 2/1993 | Nappholz et al. |
| 5,190,035 A | 3/1993 | Salo et al. |
| 5,199,424 A | 4/1993 | Sullivan et al. |
| 5,199,428 A | 4/1993 | Obel et al. |
| 5,203,326 A | 4/1993 | Collins |
| 5,209,229 A | 5/1993 | Gilli |
| 5,211,173 A | 5/1993 | Kallok et al. |
| 5,215,082 A | 6/1993 | Kallok et al. |
| 5,243,979 A | 9/1993 | Stein et al. |
| 5,243,980 A | 9/1993 | Mehra |
| 5,245,995 A | 9/1993 | Sullivan et al. |
| 5,259,373 A | 11/1993 | Gruenke et al. |
| 5,261,400 A | 11/1993 | Bardy |
| 5,275,159 A | 1/1994 | Griebel |
| 5,280,791 A | 1/1994 | Lavie |
| 5,292,338 A | 3/1994 | Bardy |
| 5,299,118 A | 3/1994 | Martens et al. |
| 5,300,106 A | 4/1994 | Dahl et al. |
| 5,306,293 A | 4/1994 | Zacouto |
| 5,314,430 A | 5/1994 | Bardy |
| 5,314,459 A | 5/1994 | Swanson et al. |
| 5,318,592 A | 6/1994 | Schaldach |
| 5,318,593 A | 6/1994 | Duggan |
| 5,318,594 A | 6/1994 | Limousin et al. |
| 5,318,597 A | 6/1994 | Hauck et al. |
| 5,330,505 A | 7/1994 | Cohen |
| 5,330,507 A | 7/1994 | Schwartz |
| 5,331,966 A | 7/1994 | Bennett et al. |
| 5,334,221 A | 8/1994 | Bardy |
| 5,356,425 A | 10/1994 | Bardy et al. |
| 5,363,842 A | 11/1994 | Mishelevich et al. |
| 5,372,606 A | 12/1994 | Lang et al. |
| 5,376,103 A | 12/1994 | Anderson et al. |
| 5,376,106 A | 12/1994 | Stahmann et al. |
| 5,377,671 A | 1/1995 | Biondi et al. |
| 5,391,187 A | 2/1995 | Freeman |
| 5,398,682 A | 3/1995 | Lynn |
| 5,404,877 A | 4/1995 | Nolan et al. |
| 5,411,525 A | 5/1995 | Swanson et al. |
| 5,411,531 A | 5/1995 | Hill et al. |
| 5,411,539 A | 5/1995 | Neisz |
| 5,417,717 A | 5/1995 | Salo et al. |
| 5,437,285 A | 8/1995 | Verrier et al. |
| 5,439,482 A | 8/1995 | Adams et al. |
| 5,441,518 A | 8/1995 | Adams et al. |
| 5,466,245 A | 11/1995 | Spinelli et al. |
| 5,468,254 A | 11/1995 | Hahn et al. |
| 5,476,485 A | 12/1995 | Weinberg et al. |
| 5,483,969 A | 1/1996 | Testerman et al. |
| 5,487,755 A | 1/1996 | Snell et al. |
| 5,490,502 A | 2/1996 | Rapoport et al. |
| 5,507,784 A | 4/1996 | Hill et al. |
| 5,520,176 A | 5/1996 | Cohen |
| 5,520,191 A | 5/1996 | Karlsson et al. |
| 5,522,382 A | 6/1996 | Sullivan et al. |
| 5,522,854 A | 6/1996 | Ideker et al. |
| 5,522,862 A | 6/1996 | Testerman et al. |
| 5,527,345 A | 6/1996 | Infinger |
| 5,531,779 A | 7/1996 | Dahl et al. |
| 5,540,734 A | 7/1996 | Zabara |
| 5,554,177 A | 9/1996 | Kieval |
| 5,578,061 A | 11/1996 | Stroetmann et al. |
| 5,590,648 A | 1/1997 | Mitchell et al. |
| 5,591,216 A | 1/1997 | Testerman et al. |
| 5,593,431 A | 1/1997 | Sheldon |
| 5,601,607 A | 2/1997 | Adams |
| 5,603,331 A | 2/1997 | Heemels et al. |
| 5,605,151 A | 2/1997 | Lynn |
| 5,606,969 A | 3/1997 | Butler et al. |
| 5,607,385 A | 3/1997 | Francischelli et al. |
| 5,620,466 A | 4/1997 | Haefner et al. |
| 5,622,178 A | 4/1997 | Gilham |
| 5,626,151 A | 5/1997 | Linden |
| 5,632,281 A | 5/1997 | Rayburn |
| 5,634,938 A | 6/1997 | Swanson et al. |
| 5,641,326 A | 6/1997 | Adams |
| 5,645,570 A | 7/1997 | Corbucci |
| 5,658,318 A | 8/1997 | Stroetmann et al. |
| 5,662,688 A | 9/1997 | Haefner et al. |
| 5,690,681 A | 11/1997 | Geddes et al. |
| 5,693,000 A | 12/1997 | Crosby et al. |
| 5,697,951 A | 12/1997 | Harpstead et al. |
| 5,697,953 A | 12/1997 | Kroll et al. |
| 5,700,282 A | 12/1997 | Zabara |
| 5,701,894 A | 12/1997 | Cherry et al. |
| 5,704,345 A | 1/1998 | Berthon-Jones |
| 5,704,365 A | 1/1998 | Albrecht et al. |
| 5,707,400 A | 1/1998 | Terry, Jr. et al. |
| 5,713,355 A | 2/1998 | Richardson et al. |
| 5,713,933 A | 2/1998 | Condie et al. |
| 5,716,377 A | 2/1998 | Rise et al. |
| 5,720,771 A | 2/1998 | Snell |
| 5,724,984 A | 3/1998 | Arnold et al. |
| 5,740,797 A | 4/1998 | Dickson |
| 5,782,883 A | 7/1998 | Kroll et al. |
| 5,792,188 A | 8/1998 | Starkweather et al. |
| 5,794,615 A | 8/1998 | Estes |
| 5,797,967 A | 8/1998 | KenKnight |
| 5,800,470 A | 9/1998 | Stein et al. |
| 5,802,188 A | 9/1998 | McDonough |
| 5,814,079 A | 9/1998 | Kieval |
| 5,826,579 A | 10/1998 | Remmers et al. |
| 5,827,326 A | 10/1998 | Kroll et al. |
| 5,839,430 A | 11/1998 | Cama |
| 5,844,680 A | 12/1998 | Sperling |
| 5,860,918 A | 1/1999 | Schradi et al. |
| 5,861,011 A | 1/1999 | Stoop |
| 5,869,970 A | 2/1999 | Palm et al. |
| 5,891,023 A | 4/1999 | Lynn |
| 5,895,414 A | 4/1999 | Sanchez-Zambrano |
| 5,902,250 A | 5/1999 | Verrier et al. |
| 5,911,218 A | 6/1999 | DiMarco |
| 5,916,239 A | 6/1999 | Geddes et al. |

(56) References Cited

U.S. PATENT DOCUMENTS

| | | |
|---|---|---|
| 5,919,141 A | 7/1999 | Money et al. |
| 5,957,861 A | 9/1999 | Combs et al. |
| 5,957,956 A | 9/1999 | Kroll et al. |
| 5,961,446 A | 10/1999 | Beller et al. |
| 5,961,450 A | 10/1999 | Merchant et al. |
| 5,964,788 A | 10/1999 | Greenhut |
| 5,970,975 A | 10/1999 | Estes et al. |
| 5,974,349 A | 10/1999 | Levine |
| 5,981,011 A | 11/1999 | Overcash et al. |
| 5,997,526 A | 12/1999 | Giba et al. |
| 6,006,134 A | 12/1999 | Hill et al. |
| 6,015,388 A | 1/2000 | Sackner et al. |
| 6,021,351 A | 2/2000 | Kadhiresan et al. |
| 6,044,297 A | 3/2000 | Sheldon et al. |
| 6,047,203 A | 4/2000 | Sackner et al. |
| 6,050,940 A | 4/2000 | Braun et al. |
| 6,058,331 A | 5/2000 | King |
| 6,059,725 A | 5/2000 | Steinschneider |
| 6,073,048 A | 6/2000 | Kieval et al. |
| 6,091,986 A | 7/2000 | Keimel |
| 6,099,479 A | 8/2000 | Christopherson et al. |
| 6,105,575 A | 8/2000 | Estes et al. |
| 6,115,628 A | 9/2000 | Stadler et al. |
| 6,117,092 A | 9/2000 | Weinstein et al. |
| 6,134,470 A | 10/2000 | Hartlaub |
| 6,141,590 A | 10/2000 | Renirie et al. |
| 6,144,866 A | 11/2000 | Miesel et al. |
| 6,148,230 A | 11/2000 | KenKnight |
| 6,148,233 A | 11/2000 | Owen et al. |
| 6,148,814 A | 11/2000 | Clemmer et al. |
| 6,155,976 A | 12/2000 | Sackner et al. |
| 6,161,042 A | 12/2000 | Hartley et al. |
| 6,168,568 B1 | 1/2001 | Gavriely |
| 6,178,349 B1 | 1/2001 | Kieval |
| 6,181,961 B1 | 1/2001 | Prass |
| 6,181,966 B1 | 1/2001 | Nigam |
| 6,200,265 B1 | 3/2001 | Walsh et al. |
| 6,205,357 B1 | 3/2001 | Ideker et al. |
| 6,212,435 B1 | 4/2001 | Lattner et al. |
| 6,227,072 B1 | 5/2001 | Ritchey et al. |
| 6,236,873 B1 | 5/2001 | Holmstrom |
| 6,240,314 B1 | 5/2001 | Plicchi et al. |
| 6,240,316 B1 | 5/2001 | Richmond et al. |
| 6,253,103 B1 | 6/2001 | Baura |
| 6,261,238 B1 | 7/2001 | Gavriely |
| 6,263,244 B1 | 7/2001 | Mann et al. |
| 6,264,606 B1 | 7/2001 | Ekwall et al. |
| 6,269,269 B1 | 7/2001 | Ottenhoff et al. |
| 6,275,727 B1 | 8/2001 | Hopper et al. |
| 6,280,462 B1 | 8/2001 | Hauser et al. |
| 6,286,508 B1 | 9/2001 | Remmers et al. |
| 6,287,264 B1 | 9/2001 | Hoffman |
| 6,292,693 B1 | 9/2001 | Darvish et al. |
| 6,292,695 B1 | 9/2001 | Webster et al. |
| 6,299,581 B1 | 10/2001 | Rapoport et al. |
| 6,303,270 B1 | 10/2001 | Flaim et al. |
| 6,306,088 B1 | 10/2001 | Krausman |
| 6,310,085 B1 | 10/2001 | Willis |
| 6,314,319 B1 | 11/2001 | Kroll et al. |
| 6,317,627 B1 | 11/2001 | Ennen |
| 6,327,499 B1 | 12/2001 | Alt |
| 6,331,536 B1 | 12/2001 | Radulovacki et al. |
| 6,351,670 B1 | 2/2002 | Kroll |
| 6,357,444 B1 | 3/2002 | Parker |
| 6,360,127 B1 | 3/2002 | Ding et al. |
| 6,361,494 B1 | 3/2002 | Lindenthaler |
| 6,361,522 B1 | 3/2002 | Scheiner et al. |
| 6,366,813 B1 | 4/2002 | DiLorenzo |
| 6,375,614 B1 | 4/2002 | Braun et al. |
| 6,375,623 B1 | 4/2002 | Gavriely |
| 6,387,907 B1 | 5/2002 | Hendricks et al. |
| 6,397,845 B1 | 6/2002 | Burton |
| 6,398,727 B1 | 6/2002 | Bui et al. |
| 6,398,739 B1 | 6/2002 | Sullivan et al. |
| 6,400,982 B2 | 6/2002 | Sweeney et al. |
| 6,409,675 B1 | 6/2002 | Turcott |
| 6,411,845 B1 | 6/2002 | Mower et al. |
| 6,411,850 B1 | 6/2002 | Kay et al. |
| 6,414,183 B1 | 7/2002 | Sakamoto et al. |
| 6,415,174 B1 | 7/2002 | Bebehani et al. |
| 6,421,557 B1 | 7/2002 | Meyer |
| 6,431,171 B1 | 8/2002 | Burton |
| 6,438,407 B1 | 8/2002 | Ousdigian et al. |
| 6,442,413 B1 | 8/2002 | Silver |
| 6,442,433 B1 | 8/2002 | Linberg |
| 6,447,459 B1 | 9/2002 | Larom |
| 6,449,503 B1 | 9/2002 | Hsu |
| 6,449,507 B1 | 9/2002 | Hill et al. |
| 6,450,957 B1 | 9/2002 | Yoshimi |
| 6,454,708 B1 | 9/2002 | Ferguson et al. |
| 6,454,719 B1 | 9/2002 | Greenhut |
| 6,463,326 B1 | 10/2002 | Hartley et al. |
| 6,467,333 B2 | 10/2002 | Lewis et al. |
| 6,468,219 B1 | 10/2002 | Njemanze |
| 6,473,644 B1 | 10/2002 | Terry, Jr. et al. |
| 6,477,420 B1 | 11/2002 | Struble et al. |
| 6,487,450 B1 | 11/2002 | Chen et al. |
| 6,491,639 B1 | 12/2002 | Turcott |
| 6,493,585 B2 | 12/2002 | Plicchi et al. |
| 6,496,715 B1 | 12/2002 | Lee et al. |
| 6,497,658 B2 | 12/2002 | Roizen et al. |
| 6,505,067 B1 | 1/2003 | Lee et al. |
| 6,511,500 B1 | 1/2003 | Rahme |
| 6,512,940 B1 | 1/2003 | Brabec et al. |
| 6,514,218 B2 | 2/2003 | Yamamoto |
| 6,522,915 B1 | 2/2003 | Ceballos et al. |
| 6,522,926 B1 | 2/2003 | Kieval et al. |
| 6,527,729 B1 | 3/2003 | Turcott |
| 6,532,388 B1 | 3/2003 | Hill et al. |
| 6,542,774 B2 | 4/2003 | Hill et al. |
| 6,544,199 B1 | 4/2003 | Morris |
| 6,547,743 B2 | 4/2003 | Brydon |
| 6,564,096 B2 | 5/2003 | Mest |
| 6,564,106 B2 | 5/2003 | Guck et al. |
| 6,572,543 B1 | 6/2003 | Christopherson et al. |
| 6,580,944 B1 | 6/2003 | Katz et al. |
| 6,584,351 B1 | 6/2003 | Ekwall |
| 6,587,727 B2 | 7/2003 | Osorio et al. |
| 6,595,927 B2 | 7/2003 | Pitts-Crick |
| 6,595,928 B2 | 7/2003 | Mansy et al. |
| 6,606,993 B1 | 8/2003 | Wiesmann et al. |
| 6,607,509 B2 | 8/2003 | Bobroff et al. |
| 6,611,713 B2 | 8/2003 | Schauerte |
| 6,615,083 B2 | 9/2003 | Kupper |
| 6,618,618 B2 | 9/2003 | Kalgren et al. |
| 6,622,041 B2 | 9/2003 | Terry, Jr. et al. |
| 6,622,046 B2 | 9/2003 | Fraley et al. |
| 6,628,986 B1 | 9/2003 | Mouchawar et al. |
| 6,628,987 B1 | 9/2003 | Hill et al. |
| 6,628,988 B2 | 9/2003 | Kramer et al. |
| 6,656,960 B2 | 12/2003 | Puskas |
| 6,658,292 B2 | 12/2003 | Kroll et al. |
| 6,662,032 B1 | 12/2003 | Gavish et al. |
| 6,679,250 B2 | 1/2004 | Walker et al. |
| 6,684,105 B2 | 1/2004 | Cohen et al. |
| 6,690,971 B2 | 2/2004 | Schauerte et al. |
| 6,694,186 B2 | 2/2004 | Bardy |
| 6,704,590 B2 | 3/2004 | Haldeman |
| 6,708,058 B2 | 3/2004 | Kim et al. |
| 6,723,055 B2 | 4/2004 | Hoffman |
| 6,741,885 B1 | 5/2004 | Park et al. |
| 6,748,252 B2 | 6/2004 | Lynn et al. |
| 6,748,271 B2 | 6/2004 | Spinelli et al. |
| 6,752,765 B1 | 6/2004 | Jensen et al. |
| 6,752,766 B2 | 6/2004 | Kowallik et al. |
| 6,760,615 B2 | 7/2004 | Ferek-Petric |
| 6,766,190 B2 | 7/2004 | Ferek-Petric |
| 6,770,029 B2 | 8/2004 | Iliff |
| 6,786,866 B2 | 9/2004 | Odagiri et al. |
| 6,799,072 B2 | 9/2004 | Ries et al. |
| 6,810,287 B2 | 10/2004 | Zhu et al. |
| 6,811,538 B2 | 11/2004 | Westbrook et al. |
| 6,824,538 B2 | 11/2004 | Chen |
| 6,850,801 B2 | 2/2005 | Kieval et al. |

(56) References Cited

U.S. PATENT DOCUMENTS

| | | |
|---|---|---|
| 6,857,428 B2 | 2/2005 | Thornton |
| 6,875,418 B2 | 4/2005 | Hampton |
| 6,884,218 B2 | 4/2005 | Olson |
| 6,892,095 B2 | 5/2005 | Salo |
| 6,910,481 B2 | 6/2005 | Kimmel et al. |
| 6,912,419 B2 | 6/2005 | Hill et al. |
| 6,922,589 B2 | 7/2005 | Stahmann et al. |
| 6,934,583 B2 | 8/2005 | Weinberg et al. |
| 6,944,579 B2 | 9/2005 | Shimizu |
| 6,959,214 B2 | 10/2005 | Pape et al. |
| 6,964,641 B2 | 11/2005 | Cho et al. |
| 6,973,349 B2 | 12/2005 | Salo et al. |
| 6,983,264 B2 | 1/2006 | Shimizu |
| 6,985,774 B2 | 1/2006 | Kieval et al. |
| 6,988,498 B2 | 1/2006 | Berthon-Jones et al. |
| 6,990,372 B2 | 1/2006 | Perron et al. |
| 6,999,817 B2 | 2/2006 | Park et al. |
| 7,010,345 B2 | 3/2006 | Hill et al. |
| 7,025,729 B2 | 4/2006 | de Chazal et al. |
| 7,027,871 B2 | 4/2006 | Burnes et al. |
| 7,039,468 B2 | 5/2006 | Freed et al. |
| 7,062,308 B1 | 6/2006 | Jackson |
| 7,072,720 B2 | 7/2006 | Puskas |
| 7,089,936 B2 | 8/2006 | Madaus et al. |
| 7,092,755 B2 | 8/2006 | Florio |
| 7,094,207 B1 | 8/2006 | Koh |
| 7,110,820 B2 | 9/2006 | Tcheng et al. |
| 7,115,097 B2 | 10/2006 | Johnson |
| 7,117,036 B2 | 10/2006 | Florio |
| 7,123,959 B2 | 10/2006 | Cates |
| 7,127,290 B2 | 10/2006 | Girouard |
| 7,130,687 B2 | 10/2006 | Cho et al. |
| 7,136,704 B2 | 11/2006 | Schulman |
| 7,142,917 B2 | 11/2006 | Fukui |
| 7,149,574 B2 | 12/2006 | Yun et al. |
| 7,154,962 B2 | 12/2006 | Cangiani et al. |
| 7,158,832 B2 | 1/2007 | Kieval et al. |
| 7,160,252 B2 | 1/2007 | Cho et al. |
| 7,162,303 B2 | 1/2007 | Levin et al. |
| 7,179,229 B1 | 2/2007 | Koh |
| 7,184,817 B2 | 2/2007 | Zhu et al. |
| 7,189,204 B2 | 3/2007 | Ni et al. |
| 7,194,313 B2 | 3/2007 | Libbus |
| 7,204,805 B2 | 4/2007 | Dean |
| 7,207,945 B2 | 4/2007 | Bardy |
| 7,212,862 B2 | 5/2007 | Park et al |
| 7,215,890 B2 | 5/2007 | Tegge, Jr. et al. |
| 7,218,964 B2 | 5/2007 | Hill et al. |
| 7,225,013 B2 | 5/2007 | Geva et al. |
| 7,225,809 B1 | 6/2007 | Bowen et al. |
| 7,231,250 B2 | 6/2007 | Band et al. |
| 7,235,050 B2 | 6/2007 | Schulman et al. |
| 7,252,640 B2 | 8/2007 | Ni et al. |
| 7,263,399 B2 | 8/2007 | Carlson |
| 7,269,459 B1 | 9/2007 | Koh |
| 7,277,757 B2 | 10/2007 | Casavant et al. |
| 7,277,761 B2 | 10/2007 | Shelchuk |
| 7,289,854 B2 | 10/2007 | Bardy et al. |
| 7,292,890 B2 | 11/2007 | Whitehurst |
| 7,302,295 B2 | 11/2007 | Stahmann et al. |
| 7,305,265 B2 | 12/2007 | Fukui |
| 7,308,311 B2 | 12/2007 | Sorensen |
| 7,310,552 B2 | 12/2007 | Puskas |
| 7,395,115 B2 | 7/2008 | Poezevera |
| 7,396,333 B2 | 7/2008 | Stahmann et al. |
| 7,400,928 B2 | 7/2008 | Hatlestsad |
| 7,428,468 B2 | 9/2008 | Takemura et al. |
| 7,460,906 B2 | 12/2008 | Libbus |
| 7,468,040 B2 | 12/2008 | Hartley et al. |
| 7,481,759 B2 | 1/2009 | Whitehurst et al. |
| 7,486,991 B2 | 2/2009 | Libbus et al. |
| 7,499,742 B2 | 3/2009 | Bolea et al. |
| 7,509,166 B2 | 3/2009 | Libbus |
| 7,542,800 B2 | 6/2009 | Libbus et al. |
| 7,570,997 B2 | 8/2009 | Lovett et al. |
| 7,570,999 B2 | 8/2009 | Libbus |
| 7,587,238 B2 | 9/2009 | Moffitt |
| 7,616,990 B2 | 11/2009 | Chavan et al. |
| 7,616,997 B2 | 11/2009 | Kieval et al. |
| 7,623,926 B2 | 11/2009 | Rossing et al. |
| 7,657,312 B2 | 2/2010 | Pastore et al. |
| 7,660,628 B2 | 2/2010 | Libbus |
| 7,662,101 B2 | 2/2010 | Lee et al. |
| 7,689,276 B2 | 3/2010 | Dobak |
| 7,747,323 B2 | 6/2010 | Libbus et al. |
| 7,769,450 B2 | 8/2010 | Libbus et al. |
| 7,778,703 B2 | 8/2010 | Gross et al. |
| 7,778,711 B2 | 8/2010 | David et al. |
| 7,840,266 B2 | 11/2010 | Libbus |
| 7,887,493 B2 * | 2/2011 | Stahmann et al. ............ 600/529 |
| 7,988,640 B2 | 8/2011 | Berthon-Jones et al. |
| 8,024,050 B2 | 9/2011 | Libbus et al. |
| 8,069,852 B2 * | 12/2011 | Burton et al. ............ 128/204.18 |
| 2001/0000346 A1 | 4/2001 | Ruton et al. |
| 2001/0018547 A1 | 8/2001 | Mechlenburg et al. |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035379 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0049476 A1 | 4/2002 | Bardy et al. |
| 2002/0052636 A1 | 5/2002 | Bardy et al. |
| 2002/0058877 A1 | 5/2002 | Baumann et al. |
| 2002/0068958 A1 | 6/2002 | Bardy et al. |
| 2002/0072773 A1 | 6/2002 | Bardy et al. |
| 2002/0082652 A1 | 6/2002 | Wentkowski et al. |
| 2002/0082658 A1 | 6/2002 | Heinrich et al. |
| 2002/0091414 A1 | 7/2002 | Bardy et al. |
| 2002/0095184 A1 | 7/2002 | Bardy et al. |
| 2002/0103510 A1 | 8/2002 | Bardy et al. |
| 2002/0107544 A1 | 8/2002 | Ostroff et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107553 A1 | 8/2002 | Hill et al. |
| 2002/0107559 A1 | 8/2002 | Sanders et al. |
| 2002/0120299 A1 | 8/2002 | Ostroff et al. |
| 2002/0138563 A1 | 9/2002 | Trivedi |
| 2002/0143264 A1 | 10/2002 | Ding et al. |
| 2002/0169384 A1 | 11/2002 | Kowallik et al. |
| 2002/0169485 A1 | 11/2002 | Pless et al. |
| 2002/0193685 A1 | 12/2002 | Mate et al. |
| 2002/0193697 A1 * | 12/2002 | Cho et al. ............ 600/529 |
| 2002/0193839 A1 | 12/2002 | Cho et al. |
| 2003/0004546 A1 | 1/2003 | Casey et al. |
| 2003/0004549 A1 | 1/2003 | Hill et al. |
| 2003/0004552 A1 | 1/2003 | Plombon et al. |
| 2003/0023175 A1 | 1/2003 | Arzbaecher et al. |
| 2003/0023184 A1 | 1/2003 | Pitts-Crick et al. |
| 2003/0036778 A1 | 2/2003 | Ostroff et al. |
| 2003/0045904 A1 | 3/2003 | Bardy et al. |
| 2003/0050538 A1 | 3/2003 | Naghavi et al. |
| 2003/0055348 A1 | 3/2003 | Chazal et al. |
| 2003/0055461 A1 | 3/2003 | Girouard et al. |
| 2003/0060848 A1 | 3/2003 | Kieval et al. |
| 2003/0069609 A1 | 4/2003 | Thompson |
| 2003/0073919 A1 | 4/2003 | Hampton et al. |
| 2003/0083241 A1 | 5/2003 | Young |
| 2003/0088027 A1 | 5/2003 | Chin et al. |
| 2003/0088278 A1 | 5/2003 | Bardy et al. |
| 2003/0088279 A1 | 5/2003 | Rissmann et al. |
| 2003/0088280 A1 | 5/2003 | Ostroff |
| 2003/0088281 A1 | 5/2003 | Ostroff et al. |
| 2003/0088282 A1 | 5/2003 | Ostroff |
| 2003/0088283 A1 | 5/2003 | Ostroff |
| 2003/0088286 A1 | 5/2003 | Ostroff et al. |
| 2003/0097153 A1 | 5/2003 | Bardy et al. |

(56) References Cited

U.S. PATENT DOCUMENTS

| | | |
|---|---|---|
| 2003/0100924 A1 | 5/2003 | Foreman et al. |
| 2003/0100925 A1 | 5/2003 | Pape et al. |
| 2003/0121519 A1 | 7/2003 | Estes et al. |
| 2003/0139780 A1 | 7/2003 | Markowitz et al. |
| 2003/0149450 A1 | 8/2003 | Mayberg |
| 2003/0149457 A1 | 8/2003 | Tcheng et al. |
| 2003/0153953 A1 | 8/2003 | Park et al. |
| 2003/0153954 A1 | 8/2003 | Park et al. |
| 2003/0153955 A1 | 8/2003 | Park et al. |
| 2003/0153956 A1 | 8/2003 | Park et al. |
| 2003/0163059 A1 | 8/2003 | Poezevera et al. |
| 2003/0171687 A1 | 9/2003 | Irie et al. |
| 2003/0176894 A1 | 9/2003 | Stahmann et al. |
| 2003/0178031 A1 | 9/2003 | Du Pen et al. |
| 2003/0187336 A1 | 10/2003 | Odagiri et al. |
| 2003/0199945 A1* | 10/2003 | Ciulla ............................ 607/48 |
| 2003/0204216 A1 | 10/2003 | Ries et al. |
| 2003/0209246 A1 | 11/2003 | Schroeder et al. |
| 2003/0212436 A1 | 11/2003 | Brown |
| 2003/0212440 A1 | 11/2003 | Boveja |
| 2003/0216789 A1 | 11/2003 | Deem et al. |
| 2004/0002742 A1 | 1/2004 | Florio |
| 2004/0030362 A1 | 2/2004 | Hill et al. |
| 2004/0039605 A1 | 2/2004 | Bardy |
| 2004/0059240 A1 | 3/2004 | Cho et al. |
| 2004/0064177 A1 | 4/2004 | Bardy et al. |
| 2004/0073093 A1 | 4/2004 | Hatlestad |
| 2004/0088015 A1 | 5/2004 | Casavant et al. |
| 2004/0088027 A1 | 5/2004 | Burnes et al. |
| 2004/0102814 A1 | 5/2004 | Sorensen et al. |
| 2004/0111040 A1 | 6/2004 | Ni et al. |
| 2004/0116981 A1 | 6/2004 | Mazar |
| 2004/0122487 A1 | 6/2004 | Hatlestad et al. |
| 2004/0122488 A1 | 6/2004 | Mazar et al. |
| 2004/0128161 A1 | 7/2004 | Mazar et al. |
| 2004/0133079 A1 | 7/2004 | Mazar et al. |
| 2004/0138719 A1 | 7/2004 | Cho et al. |
| 2004/0163648 A1 | 8/2004 | Burton |
| 2004/0176695 A1 | 9/2004 | Poezevara |
| 2004/0176809 A1 | 9/2004 | Cho et al. |
| 2004/0186523 A1 | 9/2004 | Florio |
| 2004/0210154 A1 | 10/2004 | Kline |
| 2004/0210155 A1 | 10/2004 | Takemura et al. |
| 2004/0210261 A1 | 10/2004 | King et al. |
| 2004/0215240 A1 | 10/2004 | Lovett et al. |
| 2004/0215258 A1 | 10/2004 | Lovett et al. |
| 2004/0230229 A1 | 11/2004 | Lovett et al. |
| 2004/0230230 A1 | 11/2004 | Lindstrom |
| 2004/0230243 A1 | 11/2004 | Haefner |
| 2004/0249416 A1 | 12/2004 | Yun et al. |
| 2005/0004615 A1 | 1/2005 | Sanders |
| 2005/0039745 A1 | 2/2005 | Stahmann et al. |
| 2005/0042589 A1 | 2/2005 | Hatlestad et al. |
| 2005/0043644 A1 | 2/2005 | Stahmann et al. |
| 2005/0043652 A1 | 2/2005 | Lovett et al. |
| 2005/0043772 A1 | 2/2005 | Stahmann et al. |
| 2005/0061315 A1 | 3/2005 | Lee et al. |
| 2005/0065447 A1 | 3/2005 | Lee et al. |
| 2005/0065567 A1 | 3/2005 | Lee et al. |
| 2005/0065572 A1 | 3/2005 | Hartley et al. |
| 2005/0101841 A9 | 5/2005 | Kaylor et al. |
| 2005/0107838 A1 | 5/2005 | Lovett et al. |
| 2005/0119711 A1 | 6/2005 | Cho et al. |
| 2005/0131467 A1 | 6/2005 | Boveja |
| 2005/0137645 A1 | 6/2005 | Voipio et al. |
| 2005/0142070 A1 | 6/2005 | Hartley et al. |
| 2005/0143779 A1 | 6/2005 | Libbus |
| 2005/0143787 A1 | 6/2005 | Boveja et al. |
| 2005/0145246 A1 | 7/2005 | Hartley et al. |
| 2005/0149128 A1 | 7/2005 | Heil Jr. et al. |
| 2005/0149129 A1 | 7/2005 | Libbus et al. |
| 2005/0149132 A1 | 7/2005 | Libbus |
| 2005/0149133 A1 | 7/2005 | Libbus et al. |
| 2005/0149143 A1 | 7/2005 | Libbus |
| 2005/0149155 A1 | 7/2005 | Scheiner et al. |
| 2005/0159784 A1 | 7/2005 | Arceta |
| 2005/0165323 A1 | 7/2005 | Montgomery et al. |
| 2005/0197675 A1 | 9/2005 | David et al. |
| 2005/0240240 A1 | 10/2005 | Park et al. |
| 2005/0288728 A1 | 12/2005 | Libbus et al. |
| 2006/0047333 A1 | 3/2006 | Tockman et al. |
| 2006/0079945 A1 | 4/2006 | Libbus |
| 2006/0106429 A1 | 5/2006 | Libbus et al. |
| 2006/0116737 A1 | 6/2006 | Libbus |
| 2006/0122675 A1 | 6/2006 | Libbus et al. |
| 2006/0178569 A1 | 8/2006 | Dean |
| 2006/0293714 A1 | 12/2006 | Salo et al. |
| 2007/0005114 A1 | 1/2007 | Salo et al. |
| 2007/0112388 A1 | 5/2007 | Salo |
| 2007/0150014 A1 | 6/2007 | Kramer et al. |
| 2007/0161873 A1 | 7/2007 | Ni et al. |
| 2007/0282215 A1 | 12/2007 | Ni et al. |

FOREIGN PATENT DOCUMENTS

| | | |
|---|---|---|
| EP | 0770407 | 5/1997 |
| EP | 1038498 | 9/2000 |
| EP | 15 2011 | 12/2001 |
| EP | 1172125 | 1/2002 |
| EP | 1234597 | 8/2002 |
| EP | 1304137 | 4/2003 |
| EP | 1317943 | 6/2003 |
| EP | 1486232 | 12/2004 |
| EP | 1541193 | 6/2005 |
| WO | WO 84002080 | 7/1984 |
| WO | WO 8605965 | 10/1986 |
| WO | WO 92003983 | 3/1992 |
| WO | WO 9217240 | 10/1992 |
| WO | WO 92020402 | 11/1992 |
| WO | WO 93001862 | 2/1993 |
| WO | WO 99004841 | 4/1999 |
| WO | WO 0009206 | 2/2000 |
| WO | WO 0017615 | 3/2000 |
| WO | WO 0124876 | 4/2001 |
| WO | WO 0143804 | 6/2001 |
| WO | WO 0176689 | 10/2001 |
| WO | WO 0226318 | 4/2002 |
| WO | WO 0234327 | 5/2002 |
| WO | WO 02085448 | 10/2002 |
| WO | WO 03003905 | 1/2003 |
| WO | WO 03011388 | 2/2003 |
| WO | WO 03041559 | 5/2003 |
| WO | WO 03075744 | 9/2003 |
| WO | WO 03076008 | 9/2003 |
| WO | WO 03082080 | 10/2003 |
| WO | WO 03099373 | 12/2003 |
| WO | WO 03099377 | 12/2003 |
| WO | WO 2004012814 | 2/2004 |
| WO | WO 2004062485 | 7/2004 |
| WO | WO 2004084990 | 10/2004 |
| WO | WO 2004084993 | 10/2004 |
| WO | WO 2004103455 | 12/2004 |
| WO | WO 2004105870 | 12/2004 |
| WO | WO 2004110549 | 12/2004 |
| WO | WO 2005018739 | 3/2005 |
| WO | WO 2005028029 | 3/2005 |
| WO | WO 2005042091 | 5/2005 |
| WO | WO 2005053788 | 6/2005 |
| WO | WO 2005063332 | 7/2005 |
| WO | WO 2005065771 | 7/2005 |
| WO | WO 2006031331 | 3/2006 |

OTHER PUBLICATIONS

Feb. 13, 2011, File History for U.S. Appl. No. 10/642,998.
Feb. 13, 2011, File History for U.S. Appl. No. 10/939,834.
Feb. 13, 2011, File History for U.S. Appl. No. 10/939,639.
Aircraft Noise and Sleep Disturbance: Final Report', prepared by the Civil Aviation Authority London on behalf of the Department of Trade, Aug. 1980 (CAA Report).
Alijore et al., Nightcap: Laboratory and home-based evaluation of a portable sleep monitor, 32 Psychophysiology, 32-98 (1995). Abstract only.

(56) References Cited

OTHER PUBLICATIONS

Altshule et al., The Effect of Position on Periodic Breathing in Chronic Cardiac Decomposition, New Eng. Journal of Med., vol. 259, No. 22, pp. 1064-1066, Nov. 27, 1958.

Andersen, Long-term follow-up of patients from a randomized trial of atrial versus ventricular pacing for sick-sinus syndrome, Lancet, 350(9086), Oct. 25, 1997, 1210-6.

Balaban et al., Feasibility of Screening for Sleep Apnea Using Pacemaker Impedance Sensor, NASPE (2001).

Baratz et al., Effect of Nasal Continuous Positive Airway Pressure on Cardiac Output and Oxygen Delivery in Patients With Congestive Heart Failure, 102 Chest, 1992, 397-401.

Benchimol, Cardiac hemodynamics during stimulation of the right atrium, right ventricle, and left ventricle in normal and abnormal hearts, Circulation, 33(6), Jun. 1966, 933-44.

Bevan et al., Sympathetic nerve-free vascular muscle, Journal of Pharmacology & Experimental Therapeutics, 157(1), Jul. 1967, 117-24.

Bevan et al., Postganglionic sympathetic delay in vascular smooth muscle, Journal of Pharmacology & Experimental Therapeutics, 152(2), May 1966, 211-30.

Bilgutay et al., Vagal tuning for the control of supraventricular arrhythmias, Surgical Forum, 16, 1965, 151-3. No copy available.

Bilgutay et al. A new concept in the treatment of hypertension utilizing an implantable electronical device: Baropacer. Trans. Am. Society Artificial Internal Organs. 1964. vol. 10, pp. 387-395. (No copy available).

Borst et al., Optimal frequency of carotid sinus nerve stimulation in treatment of angina pectoris, Cardiovascular Research, 8(5), Sep. 1974, 674-80. No copy available.

Bradley et al, Cardiac Output Response to Continuous Positive Airway Pressure in Congestive Heart Failure, 145 Am. Rev. Respir. Dis. 377-382 (1992).

Bradley et al., Sleep Apnea and Heart Failure, Part I: Obstructive Sleep Apnea, 107 Circulation 1671-1678 (2003).

Bradley et al., Pathophysiologic and Therapeutic Implications of Sleep Apnea in Congestive Heart Failure, 3 J. Cardiac Failure 223-240 (1996).

Braunwald et al., Carotid sinus nerve stimulation in the treatment of angina pectoris and supraventricular trachycardia, California Medicine, 112(3), Mar. 1970, 41-50.

Braunwald et al., Relief of angina pectoris by electrical stimulation of the carotid—sinus nerves, New England Journal of Medicine, 277(24), Dec. 14, 1967, 1278-83. No copy available.

Buda et al., Effect of Intrathoracic Pressure on Left Ventricular Performance, 301 Engl. J. Med. 453-459 (1979).

Calvin et al., Positive End—Expiratory Pressure (PEEP) Does Not Depress Left Ventricular Function in Patients With Pulmonary Edema, 124 Am. Rev. Respir. Dis. 121-128 (1981).

Chapleau, Contrasting effects of static and pulsatile pressure on carotid baroreceptor activity in dogs, Circulation, vol. 61, No. 5, Nov. 1987, pp. 648-658.

Coleridge et al. "The distribution, connexions and histology of baroreceptors in the pulmonary artery, with some observations on the sensory innervation of the ductus arteriosus." Physiology. May 1961. vol. 156, pp. 591-602.

Cooper et al., Neural effects on sinus rate and atrioventricular conduction produced by electrical stimulation from a transvenous electrode catheter in the canine right pulmonary artery, Circulation Research, 46(1), Jan. 1980, 48-57.

Dark et al., Breathing Pattern Abnormalities and Arterial Oxygen Desaturation During Sleep in the Congestive Heart Failure Syndrome, Chest, Jun. 1987, 6:833-6.

Dart Jr. et al., Carotid sinus nerve stimulation treatment of angina refractory to other surgical procedures, Annals of Thoracic Surgery, 11(4), Apr. 1971, 348-59. No copy available.

De Hoyos et al., Haemodynamic Effects of Continuous Positive Airway Pressure in Humans With Normal and Impaired Left Ventricular Function, 88 Clin. Sci. (Lond). 173-8 (1995).

De Landsheere et al., Effect of spinal cord stimulation on regional myocardial perfusion assessed by positron emission tomography, American Journal of Cardiology, 69(14), May 1, 1992, 1143-9.

Dunning, Electrostimulation of the Carotid Sinus Nerve in Angina Pectoris, University Department of Medicine, Binnengasthuis, Amsterdam: Printed by Royal VanGorcum, Assen, Netherlands, 1971, 1-92, No copy available.

Farrehi, Stimulation of the carotid sinus nerve in treatment of angina pectoris, American Heart Journal, 80(6), Dec. 1970, 759-65. No copy available.

Feliciano et al., Vagal nerve stimulation releases vasoactive intestinal peptide which significantly increases coronary artery blood flow, Cardiovascular Research, 40(1), Oct. 1998, 45-55.

Fromer et al., Ultrarapid subthreshold stimulation for termination of atrioventricular node reentrant tachycardia, Journal of the American College of Cardiology, 20(4), Oct. 1992, 879-83,.

Garrigue, Night Atrial Overdrive with DDD Pacing Results in a Significant Reduction of Sleep Apnea Episodes and QOL Improvement in Heart Failure Patients, Hosp. Cardiologique du Haut-Leveque, Bordeaux-Pessac, France, Abstract Session 25, p. 145.

Garrigue et al., Night Atrial Overdrive with DDD Pacing: a New Therapy for Sleep Apnea Syndrome, NASPE (2000).

Garrigue et al., Benefit of Atrial Pacing in Sleep Apnea Syndrome, 346 N. Engl. J. Med. 404-412 (2002).

Giardino et al., Respiratory Sinus Arrhythmia is Associated with the Efficiency of Pulmonary Gas Exchange in Healthy Humans, 284 Am. J. Physiol. H1585- 1591 (2003).

Gradaus et al., Nonthoracotomy Implantable Cardioverter Defibrillator Placement in Children: Use of a Subcutaneous Array Leads and Abdominally Placed Implantable Cardioverter Defibrillators in Children, J. Of Cardiovascular Electrophysiology, vol. 12, No. 3, pp. 356-360 (Mar. 2001).

Grassi et al., Baroreflex and non-baroreflex modulation of vagal cardiac control after myocardial infarction, Am J Cardiol, 84(5), Sep. 1, 1999, 525-9,.

Griffith et al., Electrical Stimulation of the Carotid Sinus Nerve in Normotensive and Renal Hypertensive Dogs, Circulation, 28, Jul.-Dec. 1963, 730, No copy available.

Hanson et al., Cardiac Gated Ventilation, 2433 SPIE 303-308 (1995).

Hartz et al., New Approach to Defibrillator Insertion, J. Thoracic Cardiovascular Surgery, vol. 97, pp. 920-922 (1989).

Henning, Effects of autonomic nerve stimulation, asynchrony, and load on dP/dtmax and on dP/dtmin, American Journal of Physiology, 260(4PT2), Apr. 1991, H1290-8.

Henning et al., Vagal nerve stimulation increases right ventricular contraction and relaxation and heart rate, Cardiovascular Research, 32(5), Nov. 1996, 846-53.

Hilton et al., Evaluation of Frequency and Time-frequency Spectral Analysis of Heart Rate Variability as a Diagnostic Marker of the Sleep Apnea Syndrome. Med Biol Eng Comput 1999 Nov, 37(6), 760-9.

Hoffman et al., Cheyne—Stokes Respiration in Patients Recovering from Acute Cardiogenic Pulmonary Edema, Chest 1990, 97:410-12.

Hood Jr. et al., Asynchronous contraction due to late systolic bulging at left ventricular pacing sites, American Journal of Physiology, 217(1), Jul. 1969, 215-21.

Ishise, Time course of sympathovagal imbalance and left ventricular dysfunction in conscious dogs with heart failure, Journal of Applied Physiology 84(4), Apr. 1998, 1234-41.

Janes, Anatomy of human extrinsic cardiac nerves and ganglia, Am J Cardiol., 57(4), Feb. 1, 1986, 299-309.

Javaheri et al., "Sleep Apnea in 81 Ambulatory Male Patients with Stable Heart Failure", from the Sleep Disorders Laboratory, Department of Veterans Affairs Medical Center, and the Department of Medicine, University of Cincinnati College of Medicine, Cincinnati, OH, pp. 2154-2159.

Jessurun et al., Coronary blood flow dynamics during transcutaneous electrical nerve stimulation for stable angina pectoris associated with severe narrowing of one major coronary artery, American Journal of Cardiology, 82(8), erratum appears in Am J Cardiol, Feb. 1999, 15;83(4):642, Oct. 15, 1998, 921-6.

Junyu et al., Posture Detection Algorithm Using Multi Axis DC-Accelerometer, Pace vol. 22, Apr. 1999, No copy available.

(56) References Cited

OTHER PUBLICATIONS

Kandel et al., Part VII: Arousal, Emotion, and Behavioral Homeostasis, In: Principles of neural science, New York:McGraw-Hill, Health Professions Division, 2000, 966-969, No copy available.
Karpawich et al., Altered cardiac histology following apical right ventricular pacing in patients with congenital atrioventricular block, Pacing Clin Electrophysiol, 22(9), Sep. 1999, 1372-7.
Kaye et al., Acute Effects of Continuous Positive Airway Pressure on Cardiac Sympathetic Tone in Congestive Heart Failure, 103 Circulation 2336-24338 (2001).
Kolettis et al., Submammary Implantation of a Cardioverter—Defibrillator with a Nonthoractomy Lead System, Am. Heart J., vol. 126, pp. 1222-1223 (Nov. 1993).
Krahn et al. Recurrent syncope. Experience with an implantable loop record. Cardiol. Clin., vol. 15(2), May 1997, pp. 316-326.
Laude et al., Effects of Breathing Pattern on Blood Pressure and Heart Rate Oscillations in Humans, 20 Clin. Exp. Pharmol. Phisiol 619, 625 (1993).
Leclercq et al., Hemodynamic importance of preserving the normal sequence of ventricular activation in permanent cardiac pacing, Am Heart J., 129(6), Jun. 1995, 1133-41.
Leng et al., Lead Configuration for Defibrillator Implantation in a Patient with Congenital Heart Disease and a Mechanical Prosthetic Tricuspid Valve, PACE, vol. 24, pp. 1291-1292, Aug. 2001.
Lenique et al., Ventilatory and Hemodynamic Effects of Continuous Positive Airway Pressure in Left Heart Failure, 155 Am. J. Respir. Crit. Care Med. 500-505 (1997).
Li, Vagal nerve stimulation markedly improves long-term survival after chronic heart failure in rats, Circulation, 109(1), Epub 2003 Dec 8, Jan. 6, 2004, 1-5.
Lugaresi et al., Snoring, 39 Electroencephalogr. Clin. Neurophysiol. 59-64 (1975). (No copy available).
Mannheimer et al., Epidural spinal electrical stimulation in severe angina pectoris, British Heart Journal, 59(1), Jan. 1988, 56-61, Abstract only.
Mannheimer et al., Transcutaneous electrical nerve stimulation in severe angina pectoris, European Heart Journal, 3(4), Aug. 1982, 297-302, Abstract only.
Mannheimer et al., Transcutaneous electrical nerve stimulation (TENS) in angina pectoris, Pain, 26(3), Sep. 1986, 291-300, Abstract only.
Mansfield, D. et al., Effects of Continuous Positive Airway Pressure on Lung Function in Patients with Chronic Obstructive Pulmonary Disease and Sleep Disordered Breathing, Respirology 365-70 (1999). Abstract only.
Mazgalev et al., Autonomic modification of the atrioventricular node during atrial fibrillation: role in the slowing of ventricular rate, Circulation 99(21), Jun. 1, 1999, 2806-14.
Mehta et al., Effects of Continuous Positive Airway Pressure on Cardiac Volumes in Patients With Ischemic and Dilated Cardiomyopathy, 161 Am. J. Respir. Crit. Care Med. 128-134 (2000).
Millar-Craig et al., Circadian variation of blood-pressure, Lancet, 1(8068), Apr. 15, 1978, 795-7, Abstract only.
Minisi et al., Regional left ventricular deafferentation increases baroreflex sensitivity following myocardial infarction, Cardiovasc Res., 58(1), Apr. 1, 2003, 136-41.
Murphy et al., Intractable angina pectoris: management with dorsal col. stimulation, Medical Journal of Australia, 146(5), Mar. 2, 1987, 260, Abstract only.
Naughton et al., Effects of Continuous Positive Airway Pressure on Intrathoracic and Left Ventricular Transmural Pressure in Congestive Heart Failure, 91 Circulation 1725-1731 (1995), pp. 1-25.
Neil et al. "Effects of electrical stimulation of the aortic nerve on blood pressure and respiration in cats and rabbits under chloralose and nembutal anaesthesia." Journal of Physiology. Sep. 1949, vol. 109 (3-4) p. 392-401.
Park & Pollock, Use of an Implantable Cardioverter Defibrillator in an Eight—Month—Old Infant with Ventricular Fibrillation Arising from a Myocardial Fibroma, PACE, vol. 22, No. 1, pp. 138-139 Jan. 1999.

Peters et al., Tempral and spatial summation caused by aortic nerve stimulation in rabbits. Effects of stimulation frequencies and amplitudes. Journal of the Autonomic Nervous System. 1989. vol. 27, pp. 193-205.
Peters et al., The principle of electrical carotid sinus nerve stimulation: a nerve pacemaker system for angina pectoris and hypertension therapy, Annals of Biomedical Engineering, 8(4-6), 1980, 445-58.
Philbin et al., Inappropriate shocks delivered by an ICD as a result of sensed potentials from a transcutaneous electronic nerve stimulation unit, Pacing & Clinical Electrophysiology, 21(10), Oct. 1998, 2010-1.
Pinsky et al., Augmentation of Cardiac Function by Elevation of Intrathoracic Pressure, 54 J. Appl. Physiol., 1983, 950-955.
Pinsky et al., Hemodynamic Effect of Cardiac Cycle—Specific Increases in Intrathoracic Pressure, 6 J. Appl. Physiol. 604-612 (1986).
Potkin et al., Effect of positive end—expiratory pressure on right and left ventricular function in patients with the adult respiratory distress syndrome, 135 Am. Rev. Respir. Dis. 307-311 (1987).
Prakash et al. Asymmetrical distribution of aortic nerve fibers in the pig, Anat Rec., 158(1), May 1967, 51-7.
Rasanen et al., Acute Myocardial Infarction Complicated by Left Ventricular Dysfunction and Respiratory Failure. The Effects of Continuous Positive Airway Pressure, 87 Chest, 1985, 158-62.
Reddel et al., Analysis of Adherence to Peak Flow Monitoring When Recording of Data is Electronic, BMJ 146-147 (2002).
Rees et al., Paroxysmal Nocturnal Dyspnoea and Periodic Respiration, The Lancet, Dec. 22-29, 1979, pp. 1315-1317.
Roche et al., Screening of Obstructive Sleep Apnea Syndrome by Heart Rate Variability Analysis, 100 Circulation 1411-1455 (1999).
Rosenqvist, The effect of ventricular activation sequence on cardiac performance during pacing, Pacing and Electro-physiology, 19(9), 1996, 1279-1286.
Rushmer, Chapter 5 — Systemic Arterial Pressure, In: Cardiovascular dynamics, Philadelphia: Saunders, 1976, 176-216.
Sato et al. "Novel Therapeutic Strategy against Central Baroreflex Failure: A Bionic Baroreflex System." Circulation. Jul. 1999 vol. 100, pp. 299-304.
Satoh et al., "Role of Hypoxic Drive in Regulation of Postapneic Ventilation During Sleep in Patients with Obstructive Sleep Apnea", Am Rev Respir Dis, 1991 Mar. 143 (3): 481-485.
Scharf, Effects of Continuous Positive Airway Pressure on Cardiac Output in Experimental Heart Failure, 19 Sleep S240-2 (1996).
Schauerte et al., Catheter stimulation of cardiac parasympathetic nerves in humans: a novel approach to the cardiac autonomic nervous system, Circulation, 104(20), Nov. 13, 2001, 2430-5.
Schauerte, Transvenous Parasympathetic Nerve Stimulation in the Inferior Vena Cava and Atrioventricular Conduction, Journal of Cardiovascular Electrophysiology, 11(1), Jan. 2000, 64-69.
Schauerte et al., Ventricular rate control during atrial fibrillation by cardiac parasympathetic nerve stimulation: a transvenous approach, Journal of the American College of Cariology, 34(7), Dec. 1999, 2043-50.
Scherlag, Endovascular Neural Stimulation via a Novel Basket Electrode Catheter: Comparison of Electrode Configurations, Journal of Interventional Cardiac Electrophysiology, 4(1), Apr. 2000, 219-224.
Schuder et al., Experimental Ventricular Defibrillation with an Automatic and Completely Implanted System, Trans. Am. Soc. Artif. Int. Organs, vol. 16, pp. 207-212 (1970).
Schuder et al., Transthoracic Ventricular Defibrillation in the Dog with Truncated and Untruncated Exponential Stimuli, IEEE Trans. On Bio-Medical Engin., vol. BME-18, No. 6, pp. 410-415 Nov. 1971.
Schuder et al., Ventricular Defibrillation in the Dog Using Implanted and Partially Implanted Electrode Systems, Am. J. Of Cardiology, vol. 33, pp. 243-247 Feb. 1974.
Smits et al., Defibrillation Threshold (DFT) Model of a Fully Subcutaneous ICD System, Europace Supplements, vol. 2, Jun. 2001 at col. 778, p. B83.
Steltner et al., Diagnosis of Sleep Apnea by Automatic Analysis of Nasal Pressure and Forced Oscillation Impedance. Am. Journal Respiratory Critical Care Medicine, vol. 165, pp. 940-944 (2002).

(56) References Cited

OTHER PUBLICATIONS

Stirbis et al., Optimizing the Shape of Implanted Artificial Pacemakers, Kaunas Medical Institute. Translated from Meditsinskaya Tekhnika, No. 6, pp. 25-27, 1986.
Takahashi, Vagal modulation of ventricular tachyarrhythmias induced by left ansae subclaviae stimulation in rabbits, Japanese Heart Journal, 39(4), Jul. 1998, 503-11.
Thrasher et al. "Unloading arterial baroreceptors causes neurogenic hypertension." American Journal Physiol. Regulatory Integrative Comp. Physiol. 2002. vol. 282, R1044-R1053.
Tkacova et al., Left Ventricular Volume in Patients with Heart Failure and Cheyne—Strokes Respiration during Sleep, Am. Journal, Respir. Crit. Care Med., vol. 156, pp. 1549-1555, 1997.
Tse et al., Long-term effect of right ventricular pacing on myocardial perfusion and function, J Am Coll Cardiol., 29(4), Mar. 15, 1997, 744-9.
Vanninen et al., Cardiac Sympathovagal Balance During Sleep Apnea Episodes, 16 Clin. Physiol. 209-216 (1996).
Veerman et al., Circadian profile of systemic hemodynamics, Hypertension, 26(1), Jul. 1995, 55-9.
Verity et al., Plurivesicular nerve endings in the pulmonary artery, Nature, 211(48), Jul. 30, 1966, 537-8.
Verity et al., Pulmonary artery innvervation: a morphopharmacologic correlation, Proceedings of the Western Pharmacology Society, 8, 1965, 57-9. no. copy available.
Verrier et al., Sleep, dreams, and sudden death: the case for sleep as an autonomic stress test for the heart, 31 Cardiovascular Research 181-211, 1996.
Verrier et al., Sleep Related Cardiovascular Risk: New Home-Based Monitoring Technology for Improved Diagnosis and Therapy, 2 A.N.E. 158-175, 1997.
Waldemark et al., Detection of Apnea using Short Window FFT Technique and Artificial Neural Network, 3390 SPIE International Society for Optical Engineering 122-133 (1998).
Wallick, Selective AV nodal vagal stimulation improves hemodynamics during acute atrial fibrillation in dogs, American Journal of Physiology—Heart & Circulatory Physiology, 281(4), Oct. 2001, H1490-7.
Waninger et al., Electrophysiological control of ventricular rate during atrial fibrillation, Pacing & Clinical Electrophysiology, 23(8), Aug. 2000, 1239-44.
Weber et al., Effects of CPAP and BIPAP on stroke volume in patients with obstructive sleep apnea syndrome. Pneumolgie Mar., 1995;49(3):233-5.
Wiggers et al., The muscular reactions of the mammalian ventricles to artificial surface stimuli, American Journal of Physiology, 1925, 346-378.
Young et al., the Occurrence of Sleep-disordered Breathing Among Middle-aged Adults, The New England Journal of Medicine, vol. 328, No. 17, pp. 1230-1235.
Zarzoso et al., Noninvasive Fetal Electrocardiogram Extraction: Blind Separation Versus Adaptive Noise Cancellation, IEEE Transactions on Biomedical Engineering, vol. 48, No. 1, pp. 12-18, Jan. 2001.
Zhang et al., Optimal ventricular rate slowing during atrial fibrillation by feedback AV nodal-selective vagal stimulation, American Journal of Physiology—Heart & Circulatory Physiology, 282(3), Mar. 2002, H1102-10.
Zhou et al., Prevention of high incidence of neurally mediated ventricular arrhythmias by afferent nerve stimulation in dogs, Circulation, 101(7), Feb. 22, 2000, 819-24.
Chapleau, Pulsatile activation of baroreceptors causes central facilitation of baroreflex, American Journal Physiol Heart Circ Physiol, Jun. 1989, 256:H1735-1741.
Gallois et al., Multi-Channel Analysis of the EEG Signals and Statistic Particularities for Epileptic Seizure Forecast, Second Joint EMBES/BMES Conference, pp. 208-215, Oct. 23-26, 2002.
Neistadt et al., Effects of electrical stimulation of the carotid sinus nerve in reversal of experimentally induced hypertension, Surgery, 61(6), Jun. 1967, 923-31, No copy available.
Schauerte et al., Transvenous parasympathetic cardiac nerve stimulation: an approach for stable sinus rate control, Journal of Cardiovascular Electrophysiology, 10(11), Nov. 1999, 1517-24.
Vanoli, Vagal stimulation and prevention of sudden death in conscious dogs with a healed myocardial infarction, Circulation Research, 68(5), May 1991, 1471-81, Abstract only.
Apr. 10, 2012 File History for U.S. Appl. No. 13/215,592.
May 26, 2011, File History for U.S. Appl. No. 10/642,998.

\* cited by examiner

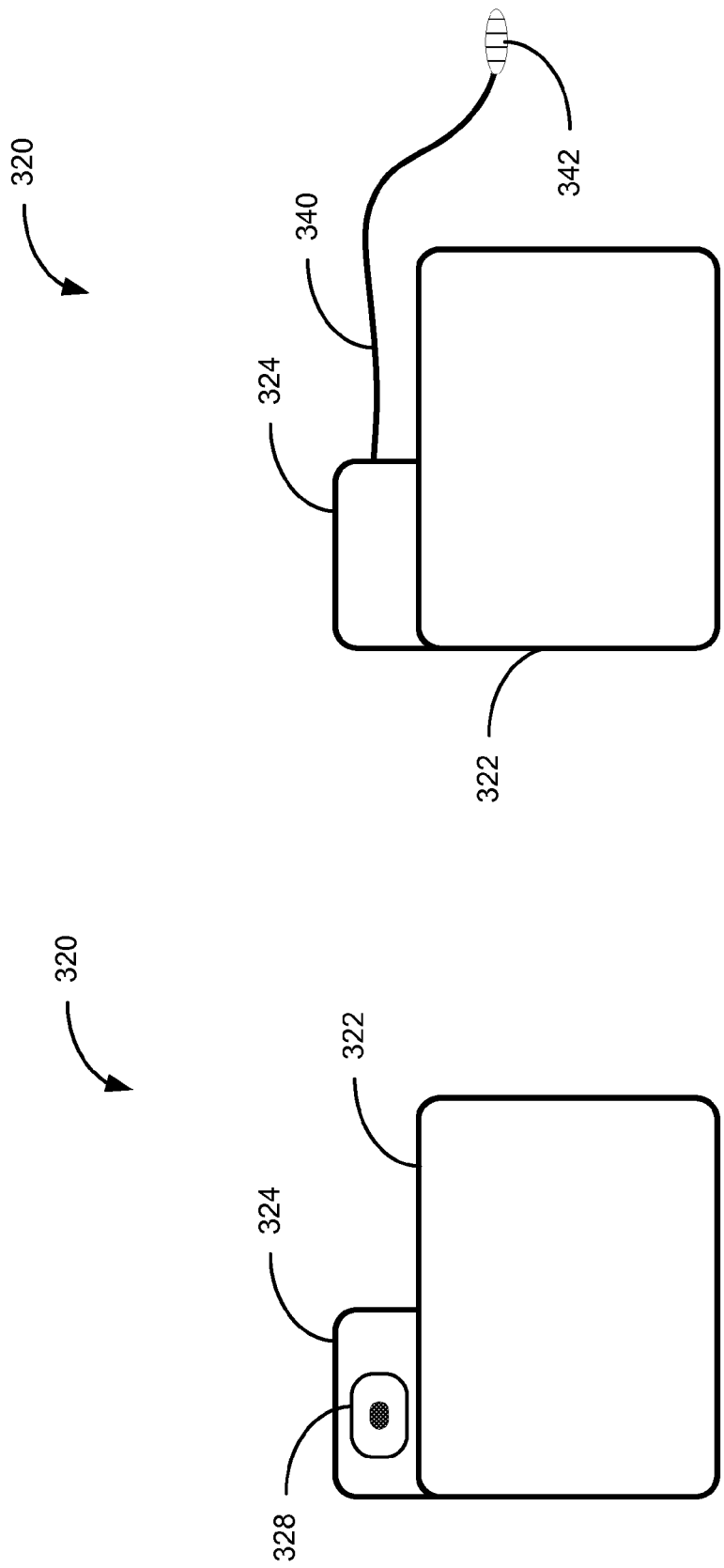

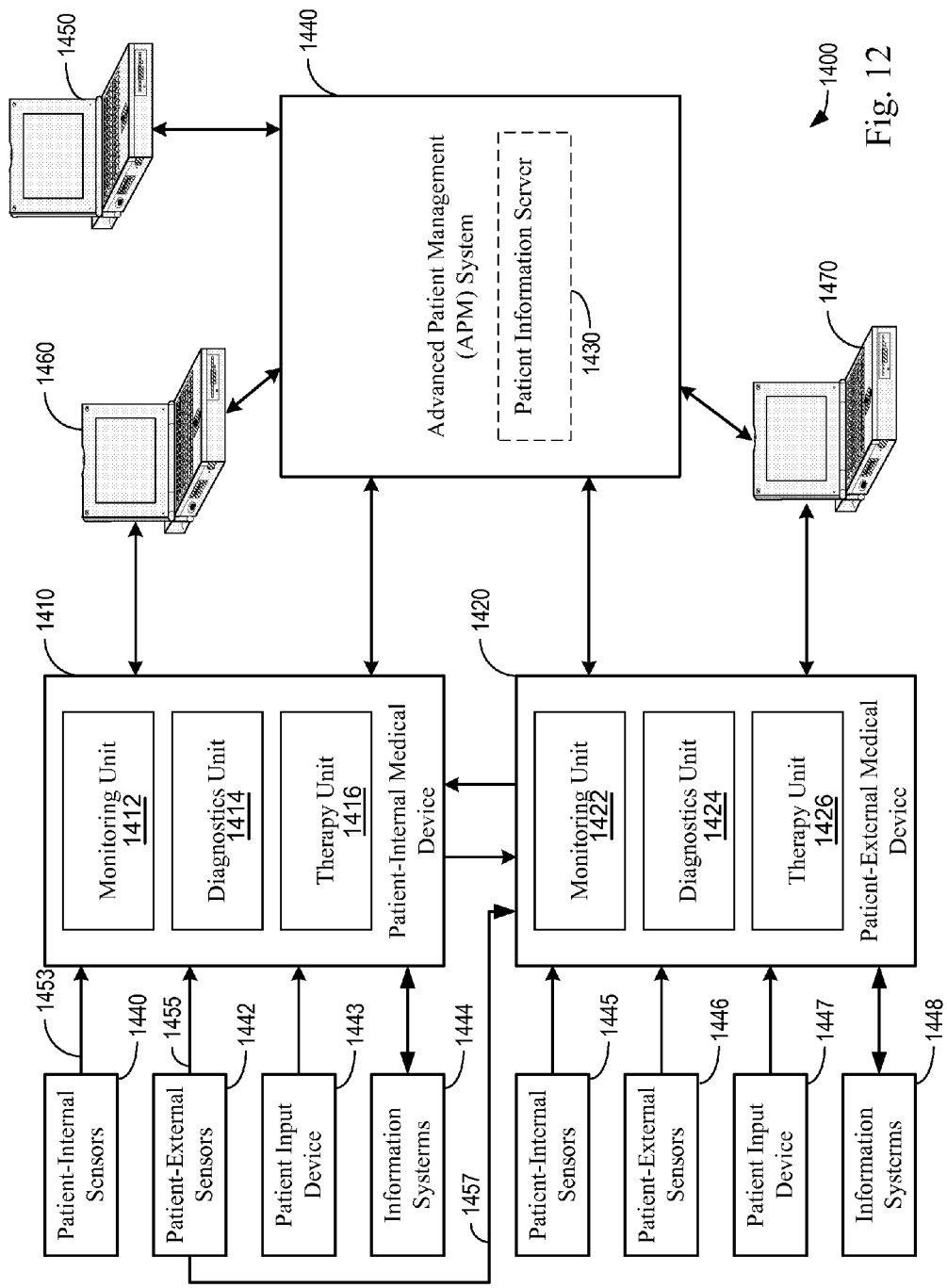

IMPLANTABLE DEVICE EMPLOYING MOVEMENT SENSING FOR DETECTING SLEEP-RELATED DISORDERS

RELATED PATENT DOCUMENTS

This application is a divisional of U.S. patent application Ser. No. 10/939,834 filed on Sep. 13, 2004, which claims the benefit of Provisional Patent Application Ser. No. 60/504,332, filed on Sep. 18, 2003, to which Applicant claims priority under 35 U.S.C. §120 and 35 U.S.C. §119(e), respectively. Both U.S. patent application Ser. No. 10/939,834 and Provisional Patent Application Ser. No. 60/504,332 are hereby incorporated herein by reference.

FIELD OF THE INVENTION

The invention relates generally to implantable medical monitoring and/or stimulation systems and methods, and more particularly to monitoring and/or stimulation systems and methods that detect electromyogram information for use in disease/pathological condition diagnosis and treatment.

BACKGROUND OF THE INVENTION

Lack of sleep and/or decreased sleep quality may have a number of causal factors including, e.g., nerve or muscle disorders, respiratory disturbances, and emotional conditions, such as depression and anxiety. Chronic, long-term sleep-related disorders e.g., chronic insomnia, sleep-disordered breathing, and sleep-related movement disorders, including restless leg syndrome (RLS), periodic limb movement disorder (PLMD) and bruxism, may significantly affect a patient's sleep quality and quality of life. Restless leg syndrome and periodic limb movement disorder are closely associated disorders also known as Myoclonus and Ekbom Syndrome, respectively. RLS and PLMD affect 2-8% of the population in the United States.

RLS and PLMD are emerging as one of the more common sleep disorders, especially among older patients. Restless leg syndrome is a disorder causing unpleasant crawling, prickling, or tingling sensations in the legs and feet and an urge to move them for relief. RLS leads to constant leg movement during the day and insomnia or fragmented sleep at night. Severe RLS is most common in elderly people, although symptoms may develop at any age. In some cases, it may be linked to other conditions such as anemia, pregnancy, or diabetes.

Many RLS patients also have PLMD, a disorder that causes repetitive jerking movements of the limbs, especially the legs. PLMD movements may be characterized, for example, by periodic flexion of one or both legs involving bending at the hip and knee with upward bending of the foot and the great toe, resembling a flexion reflex. A normal healthy person may have five of these movements per hour. The diagnosis of PLMD is given when more than five movements per hour occur. These movements cause repeated arousals and severely fragmented sleep. Because RLS patients may also suffer from sleep-related PLMD, these patients are often awakened, and their ability to return to sleep is delayed by RLS.

Both genders are affected, with a slightly higher incidence in women. These conditions are seen more commonly with advancing age. The prevalence of PLMD or RLS is 2% of the population of ages less than 30, 5% of ages 30 to 50, and 25% of ages 50-60. The highest prevalence is seen in age 65 or older, with 44% of the population affected. While usually diagnosed in older groups, these disorders may be traced to childhood. Hyperactive, fidgeting children or youths often labeled with "growing pains" may actually be showing the early manifestations of PLMD and RLS.

For both PLMD and RLS patients, sleep quality deteriorates. When a patient tries to fall asleep, the leg discomfort begins. In severe cases, patients only sleep a few hours at night, resulting in excessive daytime sleepiness and disruption of the normal daily routine. RLS and PLMD patients often complain of irritability, anxiety, and depression. The severity of RLS and/or PLMD ranges from infrequent minor discomfort to daily agony that leads some patients to contemplate suicide.

Symptoms of PLMD may come and go through the night and over the course of one's life. PLMD episodes may last a few minutes or several hours. There may be an interval of days, weeks or months between episodes. PLMD patients may experience sudden but rhythmic limb jerks occurring periodically, e.g., every 20 to 40 seconds. PLMD episodes may be seen primarily in the first third of the night, during non-REM sleep. Patients with RLS often have PLMD, but patients with PLMD do not always have RLS. Polysomnographic studies indicate that about 70% to 90% of patients with RLS have PLMD. Polysomnographic studies are also used to detect disordered breathing. Patients with RLS and/or PLMD may also have a disordered breathing disorder contributing to their deterioration of sleep quality.

Disordered breathing refers to a wide spectrum of respiratory conditions that involve disruption of the normal respiratory cycle. Although disordered breathing typically occurs during sleep, the condition may also occur while the patient is awake. Unfortunately, disordered breathing is often undiagnosed. If left untreated, the effects of disordered breathing may result in serious health consequences for the patient.

Various types of disordered respiration have been identified, including, for example, apnea, hypopnea, dyspnea, hyperpnea, tachypnea, and periodic breathing, including Cheyne-Stokes respiration (CSR). Apnea is a fairly common disorder characterized by periods of interrupted breathing. Apnea is typically classified based on its etiology.

One type of apnea, denoted obstructive apnea, occurs when the patient's airway is obstructed by the collapse of soft tissue in the rear of the throat. Central apnea is caused by a derangement of the central nervous system control of respiration. The patient ceases to breathe when control signals from the brain to the respiratory muscles are absent or interrupted. Mixed apnea is a combination of the central and obstructive apnea types.

Regardless of the type of apnea, people experiencing an apnea event stop breathing for a period of time. The cessation of breathing may occur repeatedly during sleep, sometimes hundreds of times a night and sometimes for a minute or longer. In addition to apnea, other types of disordered respiration have been identified, including hypopnea (shallow breathing), tachypnea (rapid breathing), hyperpnea (heavy breathing), and dyspnea (labored breathing). Combinations of the respiratory cycles described above may be observed, including, for example, periodic breathing and Cheyne-Stokes breathing.

Periodic breathing is characterized by cyclic respiratory patterns that may exhibit rhythmic rises and falls in tidal volume. Cheyne-Stokes respiration is a specific form of periodic breathing wherein the tidal volume decreases to zero resulting in apneic intervals. The breathing interruptions of periodic breathing and CSR may be associated with central apnea, or may be obstructive in nature. CSR is frequently observed in patients with congestive heart failure (CHF) and is associated with an increased risk of accelerated CHF progression. Because of the cardiovascular implications, therapy for respiration-related sleep disorders is of particular interest.

Disordered breathing affects a significant percentage of people. Sleep-disordered breathing is particularly prevalent and is associated with excessive daytime sleepiness, systemic hypertension, increased risk of stroke, angina and myocardial infarction. Respiratory disruption may be particularly serious for patients concurrently suffering from cardiovascular deficiencies, such as congestive heart failure.

An adequate duration and quality of sleep is required to maintain physiological homeostasis. Untreated, sleep disturbances may have a number of adverse health and quality of life consequences ranging from cognitive impairment, headaches, degradation of social and work-related activities, and increased risk of automobile and other accidents.

SUMMARY OF THE INVENTION

The present invention is directed to systems and methods for detecting sleep-related disorders involving sensing physiological signals including at least muscle movement signals. Sleep-related disorders are detected using the sensed physiological signals. The sleep-related disorders include at least an involuntary muscle movement disorder and sleep-disordered breathing. The physiological signals may include movement signals, such as electromyogram signals, at least some of which may be sensed from one or more intramuscular and/or skin/surface locations. The physiological signals may include transthoracic impedance signals, which may be sensed implantably.

Embodiments of methods of detecting sleep-related disorders may involve detecting one or more sleep stages using muscle movement signals. Methods may also involve delivering and/or controlling a therapy to treat one or more of the detected sleep-related disorders, such as a respiratory therapy, a cardiac pacing therapy, a nerve stimulation therapy, and/or a drug therapy.

Embodiments of methods of the present invention may involve detecting the sleep-related disorders patient-externally and/or patient-internally. Detecting the sleep-related disorders may involve detecting a first sleep-related disorder patient-internally and detecting a second sleep-related disorder patient-externally. Methods may further involve detecting one or more sleep stages using the muscle movement signals.

Sleep-disordered breathing may include sleep apnea, hypopnea, and/or Cheyne-Stokes respiration, and sleep-related disorders may include bruxism, periodic limb movement disorder, and/or restless leg syndrome. One or both of the physiological signals and information associated with the detected sleep-related disorders may be communicated to a patient-external processing system or an implantable medical device. Methods may further involve delivering and/or controlling a therapy to treat one or more of the detected sleep-related disorders, such as by delivering a respiratory therapy, a cardiac pacing therapy, a nerve stimulation therapy, and/or a drug therapy.

According to another embodiment, a system for detecting sleep-related disorders includes one or more movement sensors, such as electromyogram (EMG) sensors, configured for sensing (internally and/or externally) movement of skeletal musculature and a sensor configured to sense a parameter associated with sleep-disordered breathing (SDB). A processor may be communicatively coupled to the movement sensors and the SDB sensor for detecting sleep-disordered breathing based on the sensed parameter and detecting an involuntary muscle movement disorder using signals produced by the movement sensors. The processor may be disposed in an implantable housing.

The processor may be disposed in a patient-external and/or patient-internal processing system. For example, the processor may be a networked processor, a component of a cardiac rhythm management system, a component of a respiratory therapy system, and/or a component of a positive airway pressure device.

The SDB sensor and/or sleep detector may include a transthoracic impedance sensor. The sleep detector may be communicatively coupled to the processor. Conditions detected by the processor include hypopnea, bruxism, involuntary muscle movement disorder, periodic limb movement disorder, and/or restless leg syndrome. A therapy delivery system may be configured to treat the sleep-disordered breathing and involuntary muscle movement disorder. A cardiac rhythm management system, a drug delivery device, a nerve stimulation device, and/or a positive airway pressure device may be configured to treat the sleep-related disorder.

Movement sensors may include one or more accelerometers, one or more electromyogram (EMG) sensors, or a combination of these sensors. The system may include a communications interface for communicating acquired movement data and/or detection information to a patient-external and/or patient-internal processing system. Control signals may also be communicated unidirectionally or bidirectionally between the system and a remote processing system.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIGS. 1D-1G are diagrams illustrating various configurations of sensors coupled to an implanted medical device in accordance with embodiments of the invention;

FIG. 12 is a block diagram of a medical system that may be used for implementing diagnosis of sleep-related disorders using EMG information in accordance with embodiments of the invention.

Figure 1A:
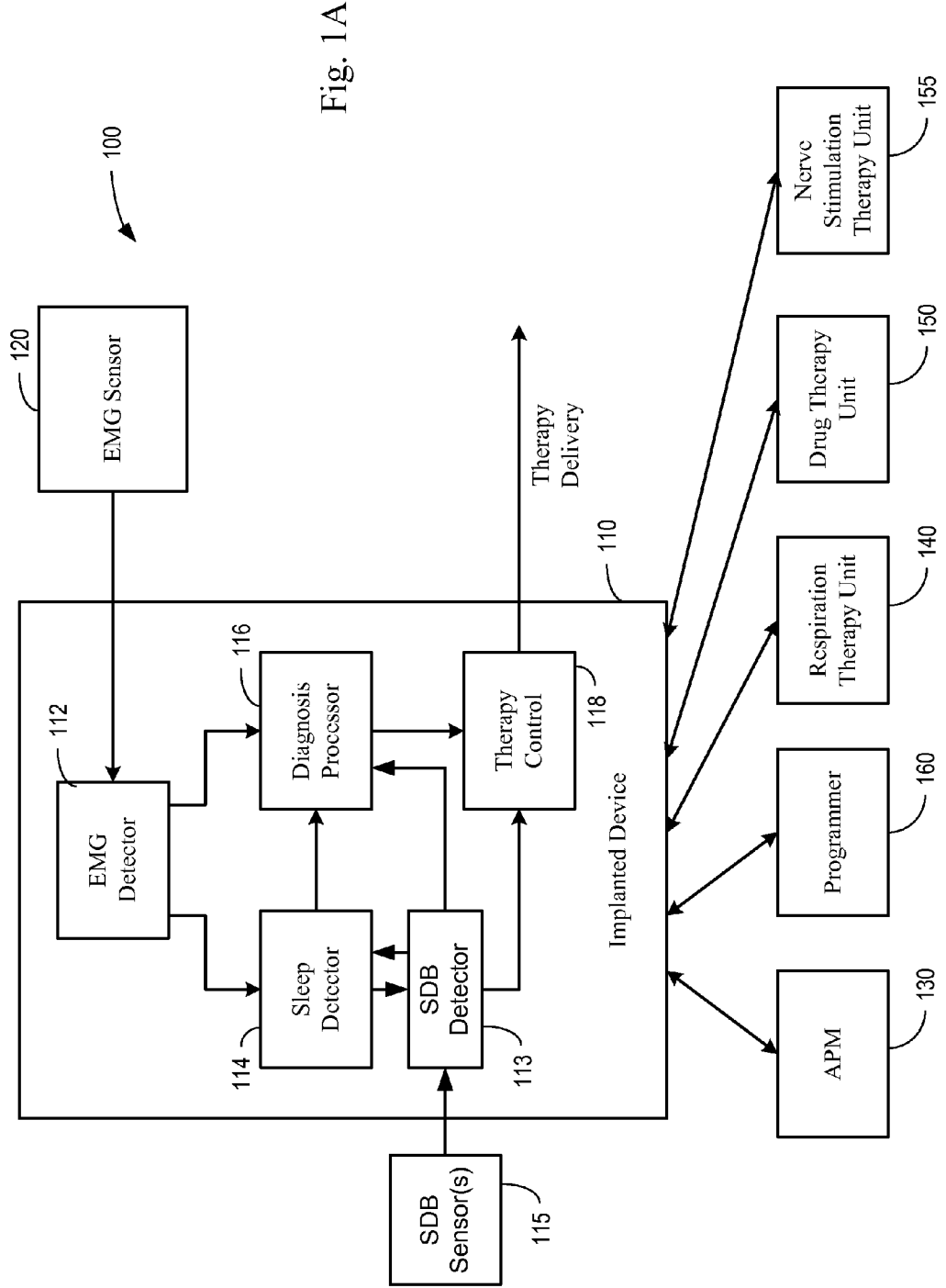
FIGS. 1A-1C are block diagrams of systems implementing diagnosis of sleep-related disorders using EMG and sleep disordered breathing information in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which are shown by way of illustration, various embodiments by which the invention may be practiced. It is to be understood that other embodiments may be utilized, and structural and functional changes may be made without departing from the scope of the invention.

Methods, devices and systems in accordance with the present invention may include one or more of the features, structures, methods, or combinations thereof described herein. It is intended that methods, devices and systems in accordance with the present invention need not include all of the features and functions described herein, but may be implemented to include selected features and functions that provide for useful structures and/or functionality.

Disorders and diseases affecting the interdependent physiological systems of the human body may be more effectively diagnosed and treated using a coordinated approach. Various embodiments of the invention are implemented using medical systems employing one or a number of patient-external and/or patient-internal medical devices. Medical devices may communicate or otherwise operate in concert or in a stand-alone manner to provide more comprehensive patient monitoring, diagnosis, and therapy.

A number of disorders, for example, sleep-disordered breathing and movement disorders such as PLMD, occur primarily while the patient is asleep. Information about the patient's sleep stage may be used to enhance sleep monitoring and/or diagnosis of a variety of disorders. In addition, it may be useful to provide a first therapy while the patient is awake and a second therapy while the patient is asleep. Detection of muscle movement, such as indicated by EMG, may be used to diagnose disorders as well as trigger the sleep-time therapy in a respiratory and/or cardiac device. Data acquired during sleep may assist in diagnosing various sleep-related disorders. The collected data may be stored, displayed, printed, or transmitted to a separate device.

The present invention is directed to systems and methods that acquire and process electromyogram signals in an implantable or partially implantable device. Information acquired from electromyogram sensors may be used in connection with patient monitoring, diagnosis, and therapy. An implantable system may incorporate EMG and SDB detection for various purposes, including disease/disorder diagnosis, sleep detection, and therapy control, among other functions. The system may include one or more EMG sensors, which may be implemented as one or more patient-internal and/or one or more patient external EMG sensors.

An electromyogram sensor detects the electrical activity of muscles during muscle activity. When muscles are active, they produce an electrical current that is proportional to the level of the muscle activity. The use of EMG sensing devices is helpful in the diagnosis of many pathological conditions.

Electromyogram sensing devices of the present invention may facilitate diagnosis of many pathological conditions. These conditions include, for example, muscular dystrophy, inflammation of muscles, pinched nerves, peripheral nerve damage (damage to nerves in the arms and legs), amyotrophic lateral sclerosis (ALS, also known as Lou Gehrig disease), myasthenia gravis, disc herniation, sleep-disordered breathing, and movement disorders such as periodic limb movement, restless limb movement, and bruxism.

Embodiments of the present invention are directed to systems and methods for screening and/or diagnosing and subsequently treating an involuntary limb movement condition, such as RLS or PLMD. In accordance with embodiments of the invention, PLMD, RLS, and/or other movement disorders such as bruxism, for example, may be diagnosed using a system that is fully or partially implantable. A partially or fully implantable device, such as a cardiac rhythm management system, may incorporate a movement detector. One or more movement sensors are coupled to the movement detector within the implantable device. The movement sensors may include any sensor or any combination of sensors capable of detecting motion and/or muscle activity associated with motion, such as accelerometers, electromyogram (EMG) sensors, and/or a combination of one or more accelerometers and one or more EMG sensors.

Signals from the movement sensors may be received and processed by the movement detector in the implantable device. The movement data may be stored in the implantable device or communicated to an external processing system, either of which may process the sensed movement information. Movement information may be processed, trended, displayed, etc. locally or remotely to detect presence of an involuntary limb movement condition.

A significant percentage of patients between the ages of 30 and 60 years experience some symptoms of disordered breathing as well as sleep-related muscle disorders. Although disordered breathing may occur while the patient is awake, it more often occurs during sleep. Sleep-disordered breathing is associated with excessive daytime sleepiness, systemic hypertension, increased risk of stroke, angina and myocardial infarction. Disordered breathing is particularly prevalent among congestive heart failure patients, and may contribute to the progression of heart failure.

Various therapies have been used to treat central and/or obstructive disordered breathing episodes, and may further be used to treat sleep-related muscle disorders. Obstructive sleep apnea has been associated with prolapse of the tongue and its surrounding structure into the pharynx, thus occluding the respiratory pathway. A commonly prescribed treatment for obstructive apnea is continuous positive airway pressure (CPAP). A CPAP device delivers air pressure through a nasal mask worn by the patient. The application of continuous positive airway pressure keeps the patient's throat open, reducing or eliminating the obstruction causing apnea. The term xPAP is used herein as a generic term for any method, system, or device useful for positive airway pressure therapy, including devices using forms of positive airway pressure, whether continuous pressure or variable pressure, as well as gas therapy and/or oxygen therapy devices.

The following discussion, with reference to FIG. 1A, describes embodiments of the invention involving disease/disorder diagnosis using an EMG detector and SDB detector in an implanted or partially implanted device. The processes and systems exemplified by these embodiments may be implemented alone or in combination with one or more processes and systems exemplified by other embodiments described herein to provide a coordinated approach to patient monitoring, diagnosis, and/or therapy. Information acquired from EMG detector and the SDB detector may be used in connection with patient monitoring, diagnosis, and therapy.

FIG. 1A illustrates an implantable system 100 incorporating EMG and SDB detection that may be used for sleep-related disease/disorder diagnosis, sleep detection, and therapy control, among other functions. In accordance with various embodiments, the system 100 includes one or more EMG sensors 120, which may be implemented as one or more patient-internal and/or one or more patient external EMG sensors.

The EMG sensor or sensors 120 may be positioned in or on the patient's body at one or more selected locations to sense electrical muscular activity at the one or more selected locations. The location of the EMG sensor or sensors 120 depends on the specific application. For example, one or more EMG sensors 120 may be positioned intramuscularly or on the surface of the skin above the muscle to detect the electrical activity of the muscle.

Intramuscular placement of EMG sensors involves inserting a needle electrode through the skin into the muscle whose electrical activity is to be measured. Because skeletal muscles are often large, several needle electrodes may need to be placed at various locations to obtain an accurate reading of muscle activity.

Signals from EMG sensor or sensors 120 may be transmitted to an EMG detector 112 of the implanted device 110 through leads or using a wireless communications link. The EMG detector 112 receives signals from the EMG sensor or sensors 120 and processes the signals for use by a diagnosis processor 116 and/or a sleep detector 114, for example.

The sleep detector 114 may use EMG information to determine various sleep stages, including REM sleep. The sleep detector 114 may also provide information from the EMG detector 112 to a sleep disordered breathing detector 113, which may use the EMG sensors 120 to detect sleep disordered breathing episodes, and/or may be coupled to one or more SDB sensors 115. It is understood that other component connection/communication architectures are possible in addition to those shown in FIG. 1A. In one implementation, one or more EMG sensors 120 may be placed on the patient's face to facilitate the detection of REM sleep. For example, one or more surface EMG sensors 120 may be placed on the patient's chin or jaw, e.g., on the mentalis muscle and/or submentalis muscle, to detect muscle atonia associated with rapid eye movement sleep.

In another implementation, one or more EMG sensors 120 and/or SDB sensors 115 may be placed on the housing, header, or lead of an implanted device 110 positioned in the pectoral region of the patient. In one configuration, the EMG sensors 120 may be used to detect atonia of the pectoral muscles during REM sleep. A sleep detector 114 may use information from the EMG detector 112 to facilitate the detection of sleep onset and offset, and to determine the various stages of sleep. Detection of sleep stages may be used, for example, in patient monitoring, diagnosis and/or therapy for various disorders, including sleep-disordered breathing. Techniques involving EMG sensors 120 positioned on an implantable device 110, such as a CRM device, are described in commonly owned U.S. Patent Publication No. 20050043652, which is incorporated by reference herein in its entirety.

The diagnosis processor 116 may use EMG-related information and SDB detection to diagnose a variety of diseases or disorders such as those listed above. Disease/disorder diagnosis may be facilitated using information acquired from the EMG detector 112 associated with the patient's muscle activity, limb movements, and respiratory motions, for example. The diagnosis processor 116 may also use information about the patient's sleep stages to aid in diagnosis.

In various embodiments, the diagnosis processor 116 may use EMG-related information and SDB detection to diagnose disorders and diseases involving muscle dysfunction, such as those caused by muscle inflammation and/or muscular dystrophy for example. The EMG information may be used to diagnose muscle weakness due to nerve disorders, including pinched nerves, peripheral nerve damage, amyotrophic lateral sclerosis (ALS), myasthenia gravis, and disc herniation, for example. The EMG- and SDB-related information may be used to diagnose a variety of movement disorders, such as periodic limb movement disorders and/or restless legs syndrome.

In other embodiments, the diagnosis processor may use information from the EMG detector 112 to diagnose disordered breathing. For example, EMG sensor or sensors 120 may be used to sense activity of the intercostal muscles produced by expansion of the chest during respiration. As previously described, the absence or presence of chest motion may be used to discriminate between central or obstructive apnea.

Alternatively, or additionally, an EMG sensor 120 may be used to detect obstructive apnea based on the degree of patency of the upper airway. Obstructive apnea is caused by upper airway occlusion due to the collapse of soft tissue in the rear of the throat. One or more EMG sensors 120 placed on the patient's chin or jaw may be used to detect muscle activity associated with tongue movement opening the upper airway.

A majority of disordered breathing episodes occur while the patient is sleeping. Sleep-related disorders such as sleep-disordered breathing may be more prevalent during particular sleep stages. Information about sleep stages, and about the frequency, number, and degree of arousals from sleep may be useful in the diagnosis of disordered breathing. Thus, a diagnosis of disordered breathing may be enhanced using sleep information from the sleep detector 114.

In yet another embodiment, diagnosis of various movement disorders, such as periodic limb movement disorder (PLMD), restless leg syndrome (RLS), and bruxism (nighttime teeth grinding) may be facilitated using one or more EMG sensors 120 coupled to an implantable device 110. Periodic limb movement disorder and restless leg syndrome are disorders that involve undesirable movements of the limbs as described in more detail below.

One or more EMG sensors 120 may be placed in or on the muscles of the limbs or other muscles to detect limb movements. For example, EMG sensors 120 placed on or in the anterior tibialis muscles may be used to identify leg movements associated with PLMD and/or RLS. EMG sensors 120 placed on the jaw may be used to identify tempomanidibular disorders such as nighttime teeth grinding or other involuntary jaw movements.

EMG-related information may be trended, stored, displayed, or transmitted from the implantable device 110 to another device. In one embodiment, information from the EMG detector 112, the sleep detector 114, and/or the diagnosis processor 116 is downloaded to a remote device, such as a programmer 160 or advanced patient management system 130 for further analysis by the remote device 130, 160 and/or the patient's physician. Information from the EMG detector, 112 the sleep detector 114, the SDB detector 113, and/or the diagnosis processor 116 may optionally be used to adjust therapy provided to a patient. Therapy provided by the implanted device 110 may be adjusted by the patient's physician or by a remote device, such as an APM 130 device or programmer 160. In one example, the patient's physician may send a command through the programmer 160 or APM device 130 to a therapy control unit 118 in the implanted device 110 to initiate, terminate, or modify therapy. In another example, the APM device 130, 160 may automatically command the implanted device 110 to adjust therapy based on analysis performed in the remote device 130, 160. In another embodiment, the therapy control unit 118 of the implanted device 110 may use information from the EMG detector 112, the sleep detector 114, and/or the diagnosis processor 116, to automatically adjust therapy provided to a patient.

The EMG-related information and SDB detection information acquired by the implantable device 110 may be transferred to other therapy devices, such as drug delivery devices 150, respiration therapy devices 140, and/or nerve stimulation therapy devices 155, such as devices that deliver a transcutaneous electric nerve stimulation therapy.

The EMG-related information acquired by the implantable device 110 may be transferred to other therapy devices (internal or external), such as drug delivery devices 150 and/or nerve stimulation therapy devices 155. For example, transcutaneous electric nerve stimulation may improve symptoms in some RLS sufferers who also have PLMD. Electrical stimulation may be applied to an area of the legs or feet, usually before bedtime, for about 15 to 30 minutes. Transcutaneous electric nerve stimulation therapy has been found to be helpful in reducing nighttime leg jerking.

The transferred information may be used to adjust the therapy delivered by one or more of the therapy devices 140, 150, 155, or used in further diagnosis and/or monitoring functions, for example. Examples of drugs useful with the drug therapy device 150 include dopamine agents (muscle relaxers), benzodiazepines (sedatives), anti-convulsants (to reduce muscle activity), and opioids (narcotics to reduce motor activity).

Although the sleep detector 114, the diagnosis processor 116, and the therapy control unit 118 are illustrated internal to the implantable device 110, it is contemplated that any or all of these components may be patient-external in alternate embodiments, and may be incorporated into other components such as the APM 130, for example. Similarly, the respiration therapy devices 140, drug delivery devices 150, and/or nerve stimulation therapy devices 155 illustrated as patient-external in FIG. 1A, may be included in the implantable device 110 in alternate embodiments. Moreover, all or particular component(s) of these devices 140, 150, 155 may be configured for patient-internal placement, patient-external placement, or both patient-internal and patient-external placement.

Figure 1B:
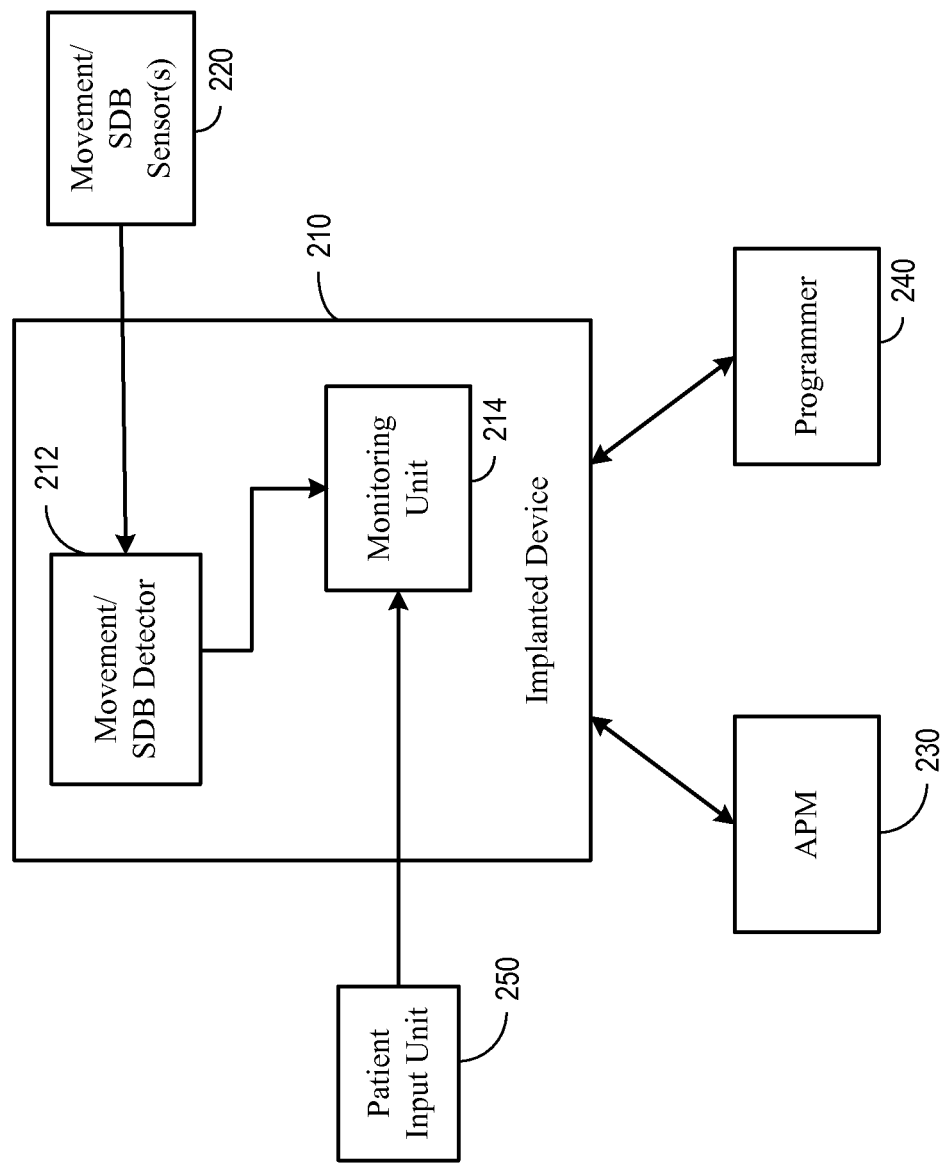
Figure 1C:
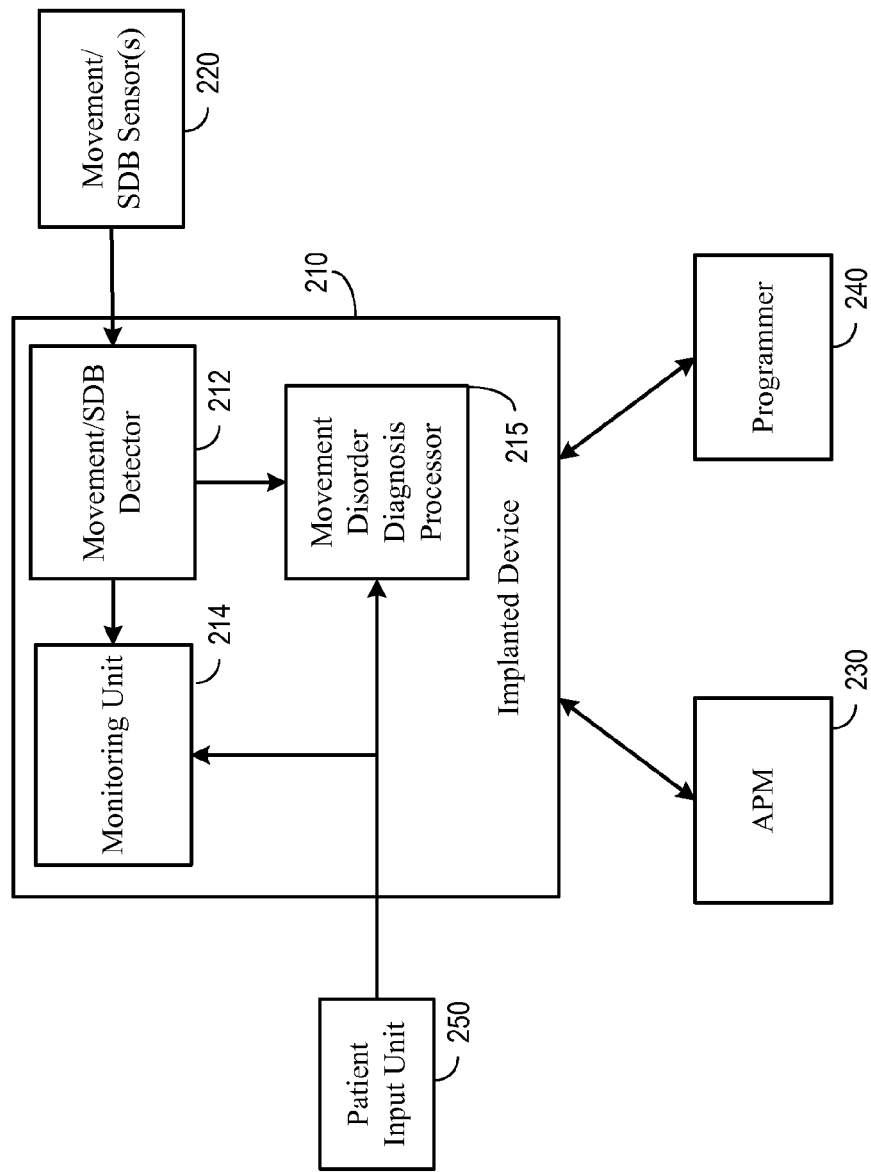
Figure 1E:
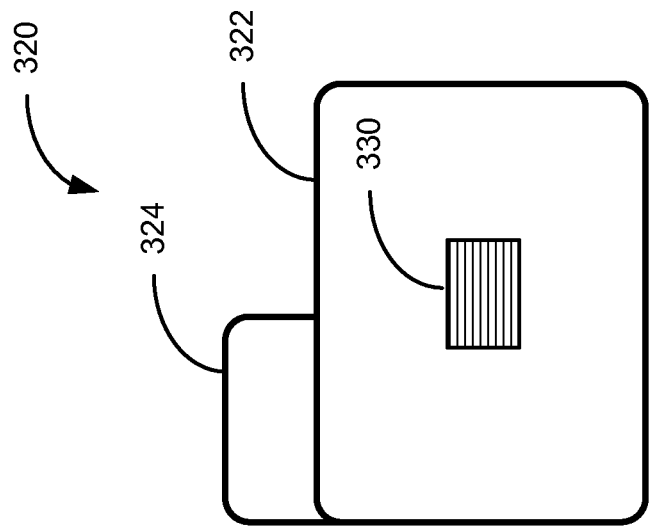
Figure 1D:
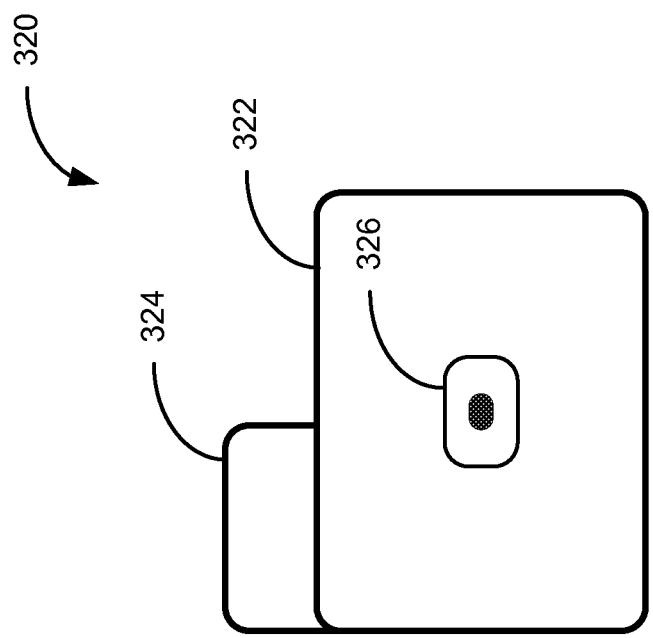

The following discussion, with reference to FIGS. 1B-1C, describes embodiments of the invention involving detection of movement disorders. The processes and systems exemplified by these embodiments may be implemented alone or in combination with one or more processes and systems exemplified by other embodiments described herein to provide a coordinated approach to patient monitoring, diagnosis, and/or therapy.

In accordance with embodiments of the invention, PLMD, RLS, and/or other movement disorders such as bruxism, for example, may be diagnosed using a system that is fully or partially implantable. FIG. 1B illustrates an implantable medical device, e.g., a CRM that incorporates a movement/SDB detector 212. One or more movement/SDB sensor(s) 220 are coupled to the movement/SDB detector 212 within an implantable device 210. Although illustrated as a single block 212 in FIG. 1B (and in FIG. 1C) for simplicity, it is understood that the movement detector and SDB detector may be represented as separate blocks. Similarly, it is understood that the movement sensor(s) and SDB sensors(s) of block 220 may be represented as separate blocks.

The movement/SDB sensor(s) 220 may include any sensor or any combination of sensors capable of detecting motion and/or muscle activity associated with motion. For example, the patient's movements may be detected using one or more accelerometers, one or more EMG sensors, and/or a combination of one or more accelerometers and one or more EMG sensors.

In one embodiment, one or more movement sensors (e.g., accelerometers and/or EMG sensors) are coupled to the patient at appropriate locations to detect movements of the extremities, e.g., limb movements, or other movements. Signals from the movement/SDB sensor(s) 220 are received and processed by a movement/SDB detector 212 in the implantable device 210. The movement/SDB detector 212 may cooperate with a memory in a monitoring unit 214 to store information about the detected movements. Movement information may be stored, trended, displayed, and/or transmitted to a separate device, such as an APM system 230 or a programmer 240 for further operations.

In another embodiment, illustrated in FIG. 1C, one or more movement/SDB sensor(s) 220 are coupled to a movement/SDB detector 212 within the implantable device 210, as previously discussed. The implantable device 210 also includes a movement disorder diagnosis processor 215 that receives movement information from the movement/SDB detector 212. The movement disorder diagnosis processor 215 evaluates the movement information to determine if the movements are consistent with various movement disorders such as RLS and/or PLMD.

In one example, the movement/SDB sensor(s) 220 may include one or more EMG sensors placed on or in the anterior tibialis. Typical EMG bursts due to PLMD movements may last between 0.5-5 seconds and may recur every 20-40 seconds, for example. The movement disorder diagnosis processor 215 may make a diagnosis of PLMD if at least about 40 EMG bursts are detected within an 8-hour sleep period, for example. Sleep disruption caused by the PLMD movements may be determined by any or a combination of the sleep detection techniques described herein, including, for example, brain wave (EEG) sensing and/or a combination of respiration (MV) and activity sensing, among others. Movement disorder diagnosis may be downloaded to a programmer 240, an APM system 230, or other therapeutic or diagnostic device.

In accordance with another embodiment of the invention, RLS diagnosis may involve patient input regarding their symptoms. For example, as illustrated in FIGS. 1B and 1C, a patient input device 250 may be used to acquire information from the patient regarding the patient's perception of symptoms. The patient may be prompted to rate their symptoms on a scale of 0 to 4, or some other scale, for example with a lower number representing fewer RLS symptoms and higher number representing greater RLS symptoms, for example. The patient input may be acquired using the patient input device 250 over a period of days, for example, about three days to about nine days to establish a diagnosis. Patient input through the patient input device 250 may also be acquired after diagnosis and/or treatment, for example to assess status of the disorder or the efficacy of treatment.

For example, if the patient input is acquired over a period of six days, the maximum score is 24, i.e., a score of four for each or six days. In this scenario, a score greater than about 12 suggests a diagnosis of severe RLS. A score of about six to about twelve suggests a diagnosis of moderate RLS.

In the embodiment illustrated in FIG. 1B, information about SDB and RLS symptoms may be acquired by the patient input device 250 and transmitted to an APM device 230, the programmer 240, or other device for monitoring, display, storage, evaluation, and/or diagnosis. In the embodiment illustrated in FIG. 1C, the information acquired by the patient input device 250, along with the movement information, may be used by the movement disorder diagnosis processor 215 in the implantable device 210 to make a diagnosis of RLS.

Embodiments of the present invention are directed to methods and systems for diagnosis of SDB and movement disorders such as PLMD and RLS. RLS diagnosis may be complicated due to the symptom based nature of the RLS diagnosis. The use of patient input through a patient-input device provides a system for collection of symptom based information. Because PLMD and RLS are related disorders, the diagnosis of PLMD through movement detection techniques described herein may be used to enhance the RLS diagnosis.

Use of the methods and systems of the invention may reduce the need for in-clinic sleep studies typically used for movement disorder diagnosis. Further, daily measurements may be made over a number of days, which is not practical for in-clinic studies. Earlier and more frequent diagnosis of movement disorders may be enabled using the systems and methods of the invention.

FIGS. 1D-1G illustrate various configurations of a movement sensor, such as an EMG sensor, mechanically coupled to an implanted medical device 320, such as an implantable pacemaker or implantable cardioverter/defibrillator in accordance with embodiments of the invention, which may be useful for diagnosing diseases such as sleep-related muscle disorders. The implantable medical device 320 may include a housing 322 enclosing the medical device circuitry and a header 324 for coupling a lead system 340 to the circuitry of the medical device 320.

A movement sensor may be implemented, for example, to include an EMG sensor that employs one or more EMG electrodes 326 or a force responsive sensor 330 positioned on the housing 322 of the medical device 320 as illustrated in FIGS. 1F and 1G, respectively. FIG. 1F illustrates one or more EMG electrodes 328 positioned on the header 324 of the medical device 320. Alternatively, a movement sensor 342 (e.g., one that includes one or more EMG electrodes or a strain gauge) may be positioned on the lead system 340 or may be coupled to the housing 322 through a catheter or lead system 340, such as by using the header 324, as illustrated in FIG. 1G.

Figure 2:
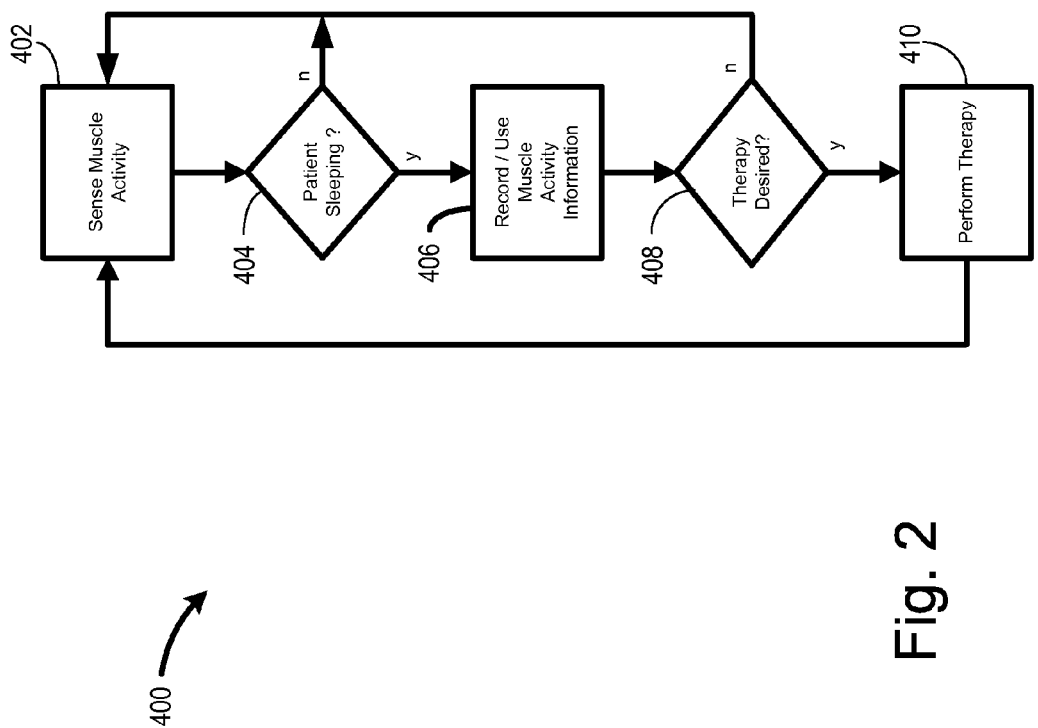
FIG. 2 is a flow chart illustrating an EMG based algorithm in accordance with embodiments of the invention.

FIG. 2 illustrates a method 400 of implantably sensing and detecting movement useful for diagnosing sleep-related muscle disorders and sleep disordered breathing. A muscle activity signal is sensed at a block 402. Muscle activity may be sensed, for example, using EMG sensors, accelerometers, or other sensors suitable for determining patient movement. A determination block 404 is used to decide if the patient is sleeping. If determination 404 concludes that the patient is not sleeping, the method 400 loops back to the beginning.

If the patient is determined to be sleeping at block 404, the muscle activity sensed at block 402 provides information recorded at block 406. For example, date, time, sensor data, sense signal amplitudes or other information may be useful for updating, developing, and/or determining an muscle disorder index, a diagnosis, a sleep-related muscle activity history, and other parameters useful for patient diagnosis and treatment. The information recorded at block 406 may be useful, for example, to predict, verify, classify, and/or determine the existence of a sleep-related muscle disorder and sleep disordered breathing.

If intervention and/or treatment is desired at determination block 408, the intervention and/or treatment may be performed at block 410 before re-starting the method 400. For example, the intervention at block 410 may be the automatic activation of a medical process, modification of a disordered breathing therapy, notification to a patient-external device and/or a physician, or other desirable action.

Figure 3:
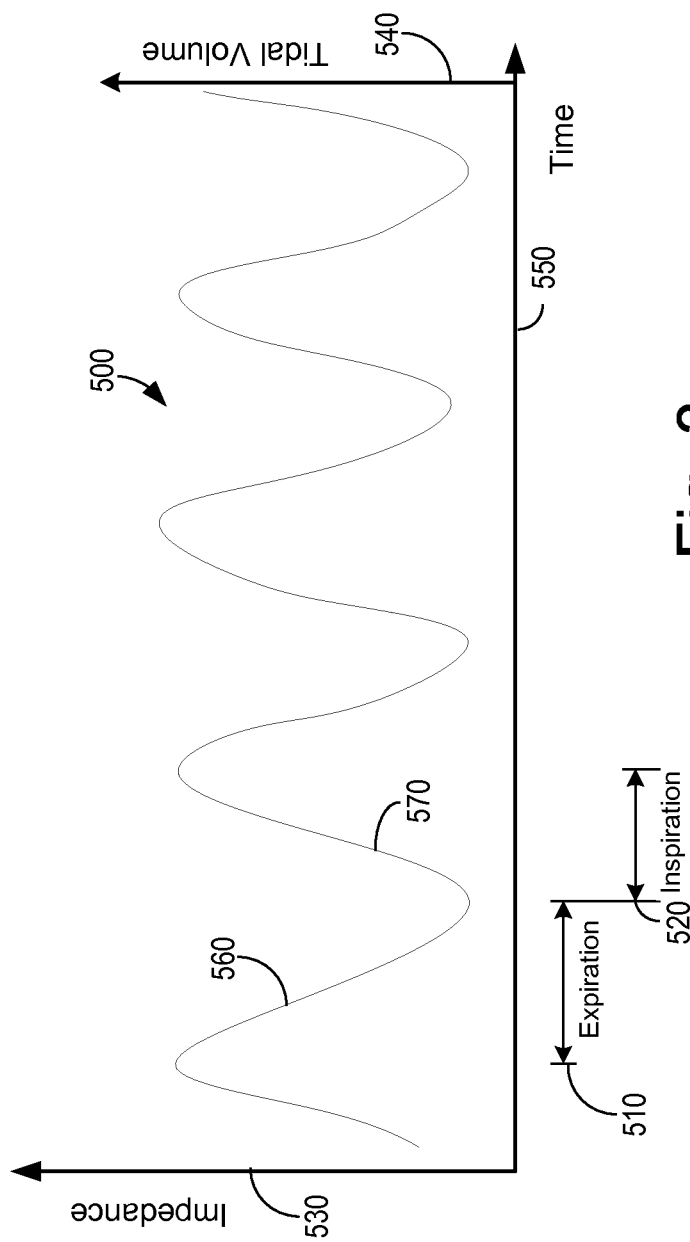
FIG. 3 is a graph of a normal respiration signal measured by a transthoracic impedance sensor that may be utilized for implementing diagnosis of sleep-related disorders in accordance with embodiments of the invention.

Referring now to FIG. 3, an impedance signal 500 is illustrated, which is useful for determining sleep, sleep state, and sleep disordered breathing. The impedance signal 500 may be developed, for example, from an impedance sense electrode in combination with a CRM device. The impedance signal 500 is proportional to the transthoracic impedance, illustrated as an Impedance 530 on the abscissa of the left side of the graph in FIG. 3.

The impedance 530 increases 570 during any respiratory inspiration 520 and decreases 560 during any respiratory expiration 510. The impedance signal 500 is also proportional to the amount of air inhaled, denoted by a tidal volume 540, illustrated on the abscissa of the right side of the graph in FIG. 3. The variations in impedance during respiration, identifiable as the peak-to-peak variation of the impedance signal 500, may be used to determine the respiration tidal volume 540. Tidal volume 540 corresponds to the volume of air moved in a breath, one cycle of expiration 510 and inspiration 520. A minute ventilation may also be determined, corresponding to the amount of air moved per a minute of time 550 illustrated on the ordinate of the graph in FIG. 3.

Breathing disorders may be determined using the impedance signal 530. During non-REM sleep, a normal respiration pattern includes regular, rhythmic inspiration-expiration cycles without substantial interruptions. When the tidal volume of the patient's respiration, as indicated by the transthoracic impedance signal, falls below a hypopnea threshold, then a hypopnea event is declared. For example, a hypopnea event may be declared if the patient's tidal volume falls below about 50% of a recent average tidal volume or other baseline tidal volume value. If the patient's tidal volume falls further to an apnea threshold, e.g., about 10% of the recent average tidal volume or other baseline value, an apnea event is declared.

An adequate quality and quantity of sleep is required to maintain physiological homeostasis. Prolonged sleep deprivation or periods of highly fragmented sleep ultimately has serious health consequences. Chronic lack of sleep may be associated with various cardiac or respiratory disorders affecting a patient's health and quality of life. Methods and systems for collecting and assessing sleep quality data are described in commonly owned U.S. Patent Publication No. 20050042589, and incorporated herein by reference. Evaluation of the patient's sleep patterns and sleep quality may be an important aspect of providing coordinated therapy to the patient, including respiratory and cardiac therapy.

Figure 4:
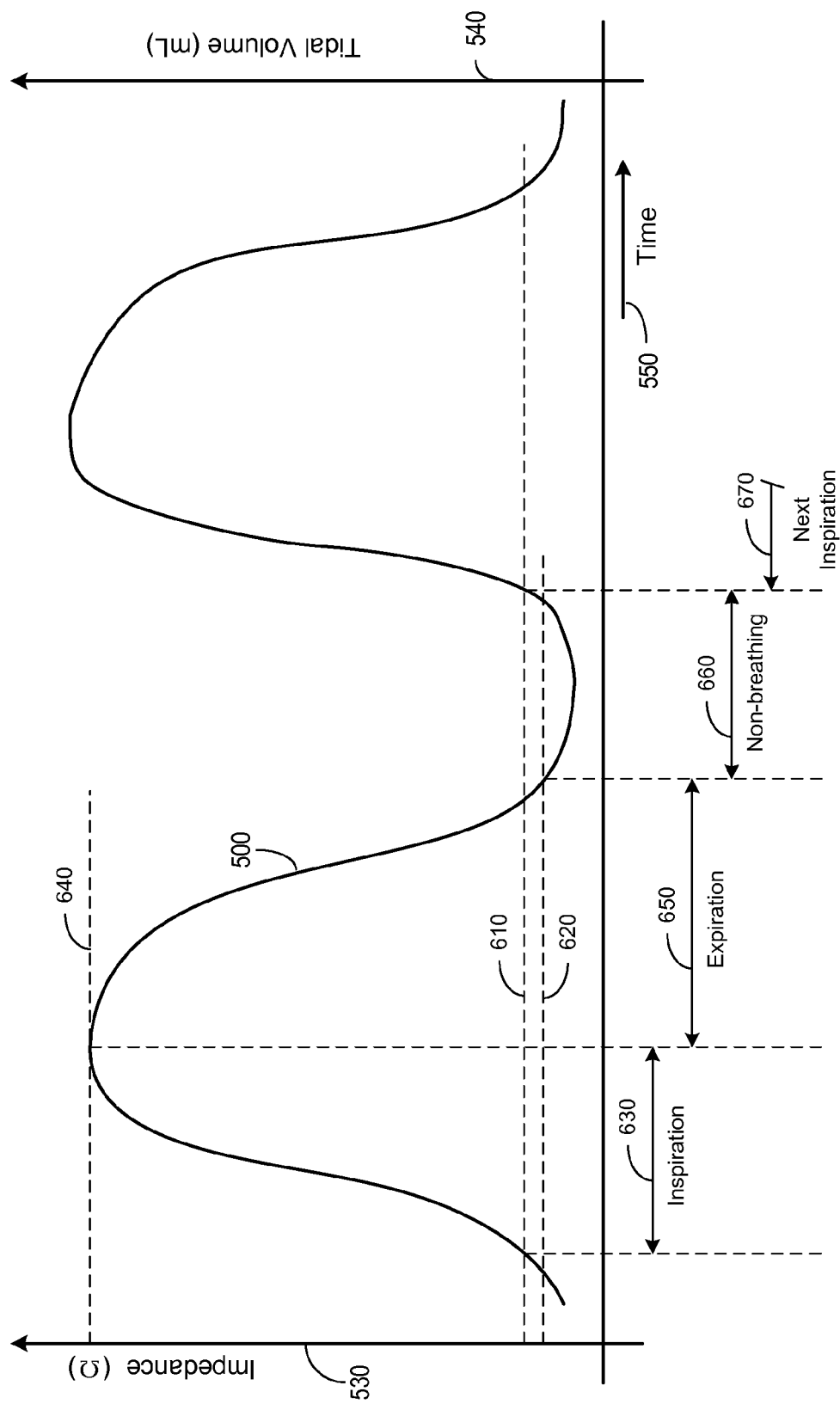
FIG. 4 is a respiration signal graph illustrating respiration intervals used for disordered breathing detection according to embodiments of the invention.
Figure 5:
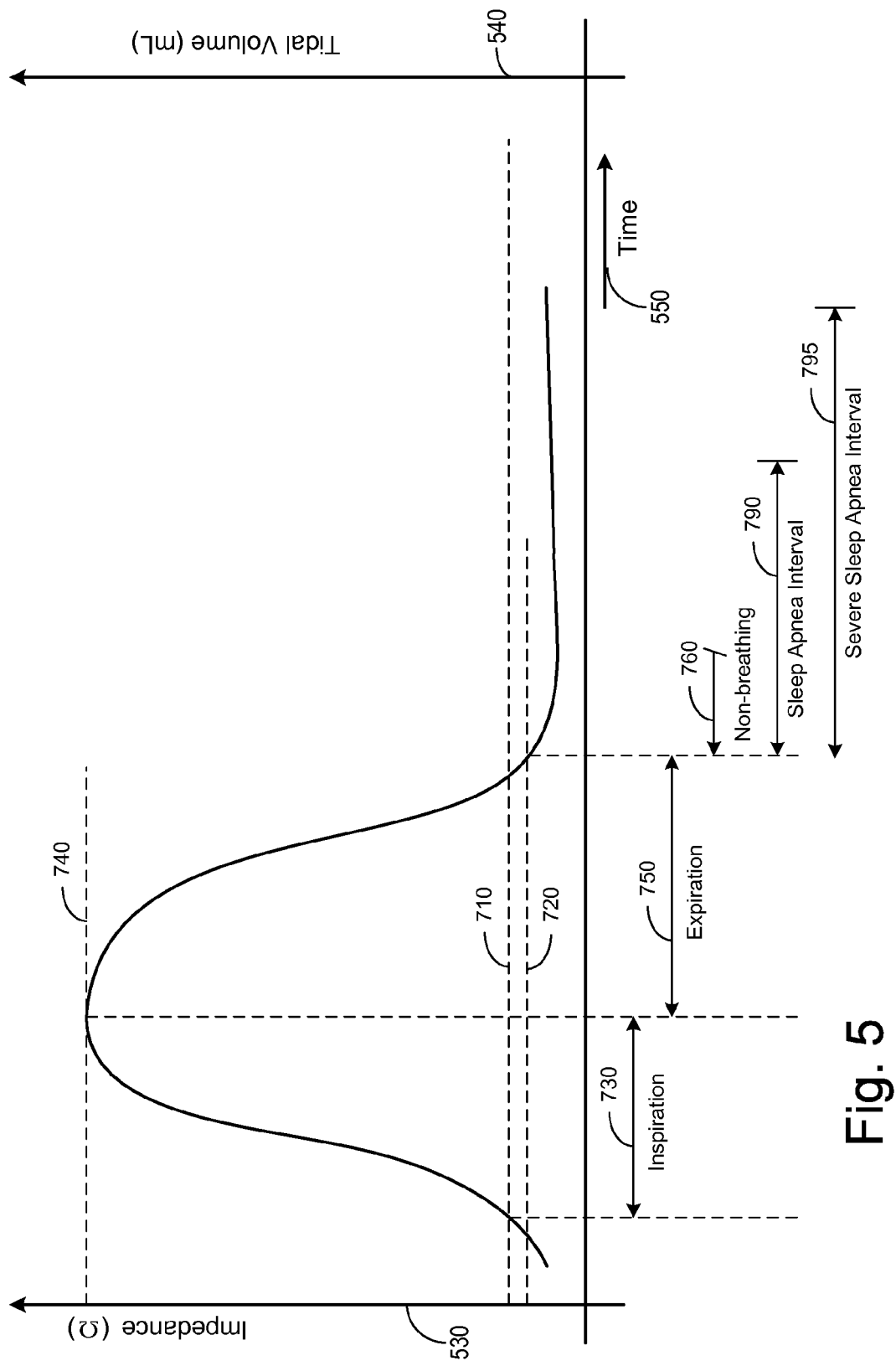
FIG. 5 is a graph of a respiration signal illustrating various intervals that may be used for detection of apnea in accordance with embodiments of the invention.
Figure 6:
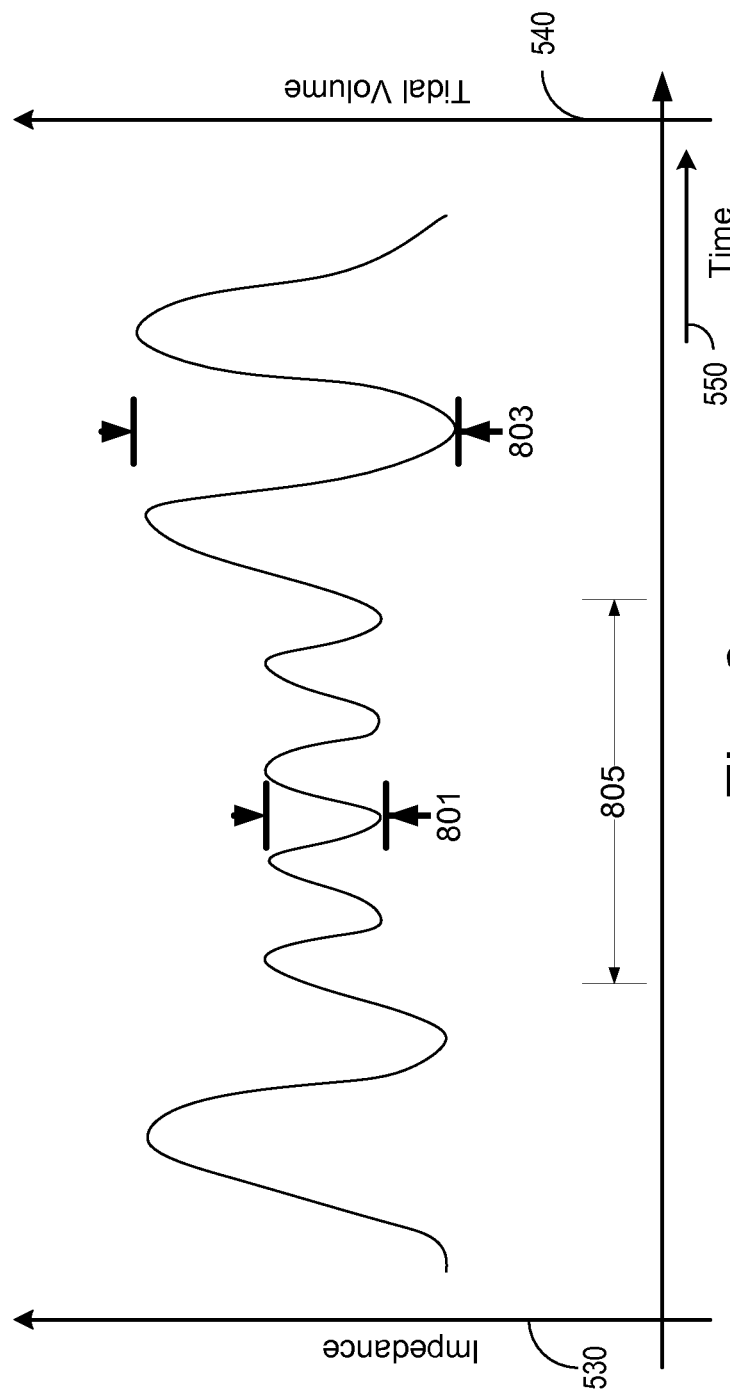
FIG. 6 is a respiration graph illustrating abnormally shallow respiration utilized in detection of disordered breathing in accordance with embodiments of the invention.

FIGS. 4-6 are graphs of transthoracic impedance and tidal volume, similar to FIG. 3 previously described. As in FIG. 3, FIGS. 4-6 illustrate the impedance signal 500 proportional to the transthoracic impedance, again illustrated as Impedance 530 on the abscissa of the left side of the graphs in FIGS. 4-6. The impedance 530 increases during any respiratory inspiration 520 and decreases during any respiratory expiration 510. As before, the impedance signal 500 is also proportional to the amount of air inhaled, denoted the tidal volume 540, illustrated on the abscissa of the right side of the graph in FIGS. 4-6. The magnitude of variations in impedance and tidal volume during respiration are identifiable as the peak-to-peak variation of the impedance signal 500.

FIG. 4 illustrates respiration intervals used for disordered breathing detection useful in accordance with embodiments of the invention. Detection of disordered breathing may involve defining and examining a number of respiratory cycle intervals. A respiration cycle is divided into an inspiration period corresponding to the patient inhaling, an expiration period, corresponding to the patient exhaling, and a non-breathing period occurring between inhaling and exhaling. Respiration intervals are established using an inspiration threshold 610 and an expiration threshold 620. The inspiration threshold 610 marks the beginning of an inspiration period 630 and is determined by the transthoracic impedance signal 500 rising above the inspiration threshold 610. The inspiration period 630 ends when the transthoracic impedance signal 500 is a maximum 640. The maximum transthoracic impedance signal 640 corresponds to both the end of the inspiration interval 630 and the beginning of an expiration interval 650. The expiration interval 650 continues until the transthoracic impedance 500 falls below an expiration threshold 620. A non-breathing interval 660 starts from the end of the expiration period 650 and continues until the beginning of a next inspiration period 670.

Detection of sleep disordered breathing events such as sleep apnea and severe sleep apnea is illustrated in FIG. 5. The patient's respiration signals are monitored and the respiration cycles are defined according to an inspiration 730, an expiration 750, and a non-breathing 760 interval as described in connection with FIG. 4. A condition of sleep apnea is detected when a non-breathing period 760 exceeds a first predetermined interval 790, denoted the sleep apnea interval. A condition of severe sleep apnea is detected when the non-breathing period 760 exceeds a second predetermined interval 795, denoted the severe sleep apnea interval. For example, sleep apnea may be detected when the non-breathing interval exceeds about 10 seconds, and severe sleep apnea may be detected when the non-breathing interval exceeds about 20 seconds.

Hypopnea is a condition of sleep disordered breathing characterized by abnormally shallow breathing. FIG. 6 is a graph of tidal volume derived from transthoracic impedance measurements. The graph of FIG. 6 illustrating the tidal volume of a hypopnea episode may be compared to the tidal volume of a normal breathing cycle illustrated previously in FIG. 2, which illustrated normal respiration tidal volume and rate. As shown in FIG. 6, hypopnea involves a period of abnormally shallow respiration, possible at an increased respiration rate.

Hypopnea is detected by comparing a patient's respiratory tidal volume 803 to a hypopnea tidal volume 801. The tidal volume for each respiration cycle may be derived from transthoracic impedance measurements acquired in the manner described previously. The hypopnea tidal volume threshold may be established by, for example, using clinical results providing a representative tidal volume and duration of hypopnea events. In one configuration, hypopnea is detected when an average of the patient's respiratory tidal volume taken over a selected time interval falls below the hypopnea tidal volume threshold. Furthermore, various combinations of hypopnea cycles, breath intervals, and non-breathing intervals may be used to detect hypopnea, where the non-breathing intervals are determined as described above.

In FIG. 6, a hypopnea episode 805 is identified when the average tidal volume is significantly below the normal tidal volume. In the example illustrated in FIG. 6, the normal tidal volume during the breathing process is identified as the peak-to peak value identified as the respiratory tidal volume 803. The hypopnea tidal volume during the hypopnea episode 805 is identified as hypopnea tidal volume 801. For example, the hypopnea tidal volume 801 may be about 50% of the respiratory tidal volume 803. The value 50% is used by way of example only, and determination of thresholds for hypopnea events may be determined as any value appropriate for a given patient.

In the example above, if the tidal volume falls below 50% of the respiratory tidal volume 803, the breathing episode may be identified as a hypopnea event, originating the measurement of the hypopnea episode 805.

Figure 7:
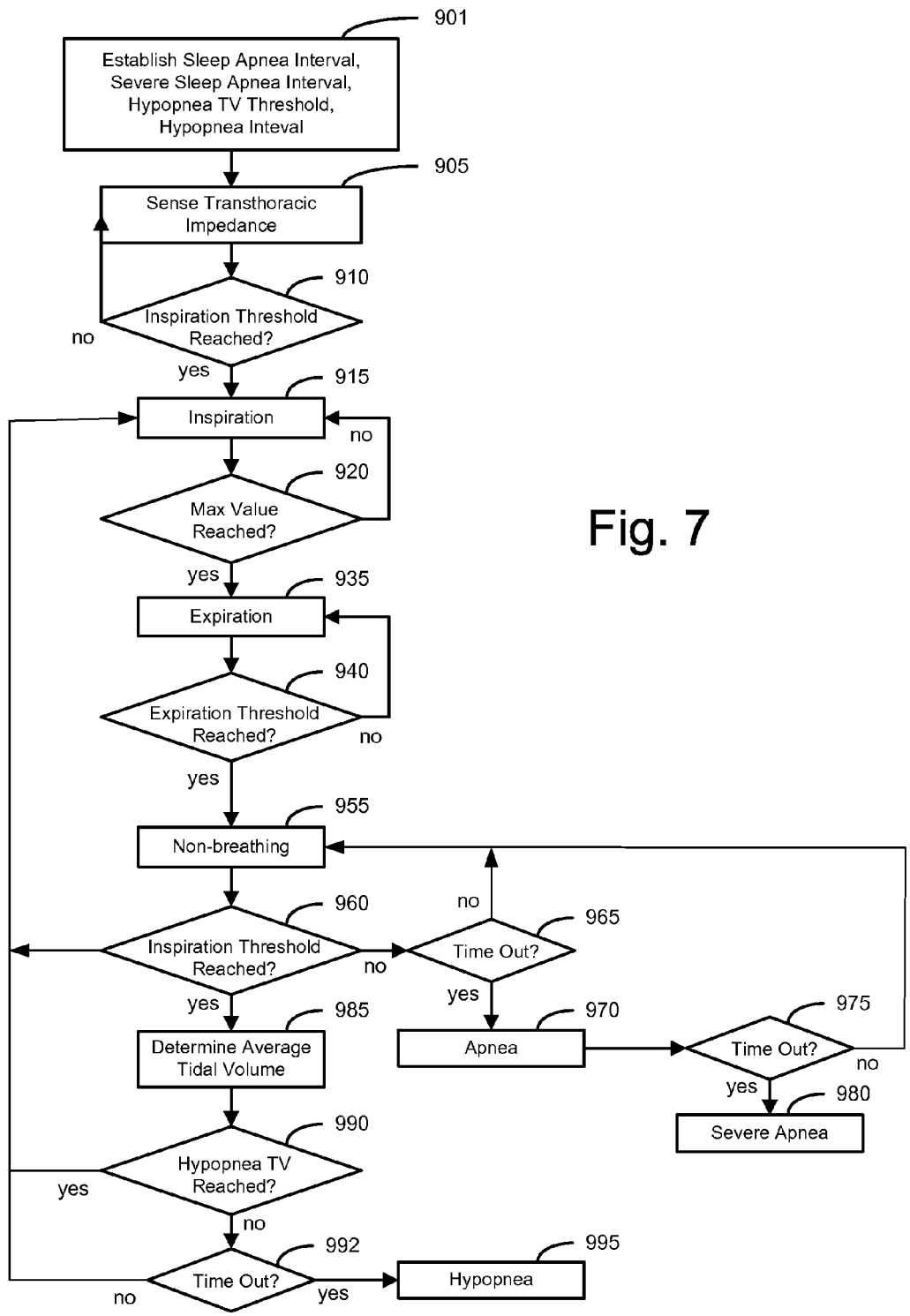
FIG. 7 is a flow chart illustrating a method of apnea and/or hypopnea detection useful for implementing diagnosis of sleep-related disorders according to embodiments of the invention.

FIG. 7 is a flow chart illustrating a method of apnea and/or hypopnea detection useful in accordance with embodiments of the invention. Various parameters are established 901 before analyzing the patient's respiration for disordered breathing episodes, including, for example, inspiration and expiration thresholds, sleep apnea interval, severe sleep apnea interval, and hypopnea tidal volume (TV) threshold.

The patient's transthoracic impedance is measured 905 as described in more detail above. If the transthoracic impedance exceeds 910 the inspiration threshold, the beginning of an inspiration interval is detected 915. If the transthoracic impedance remains below 910 the inspiration threshold, then the impedance signal is checked 905 periodically until inspiration 915 occurs.

During the inspiration interval, the patient's transthoracic impedance is monitored until a maximum value of the transthoracic impedance is detected 920. Detection of the maximum value signals an end of the inspiration period and a beginning of an expiration period 935.

The expiration interval is characterized by decreasing transthoracic impedance. When, at determination 940, the transthoracic impedance falls below the expiration threshold, a non-breathing interval is detected 955.

If the transthoracic impedance determination 960 does not exceed the inspiration threshold within a first predetermined interval, denoted the sleep apnea interval 965, then a condition of sleep apnea is detected 970. Severe sleep apnea 980 is detected if the non-breathing period extends beyond a second predetermined interval, denoted the severe sleep apnea interval 975.

When the transthoracic impedance determination 960 exceeds the inspiration threshold, the tidal volume from the peak-to-peak transthoracic impedance is calculated, along with a moving average of past tidal volumes 985. The peakto-peak transthoracic impedance provides a value proportional to the tidal volume of the respiration cycle. This value is compared at determination 990 to a hypopnea tidal volume threshold. If, at determination 990, the peak-to-peak transthoracic impedance is consistent with the hypopnea tidal volume threshold for a predetermined time 992, then a hypopnea cycle 995 is detected.

Figure 8:
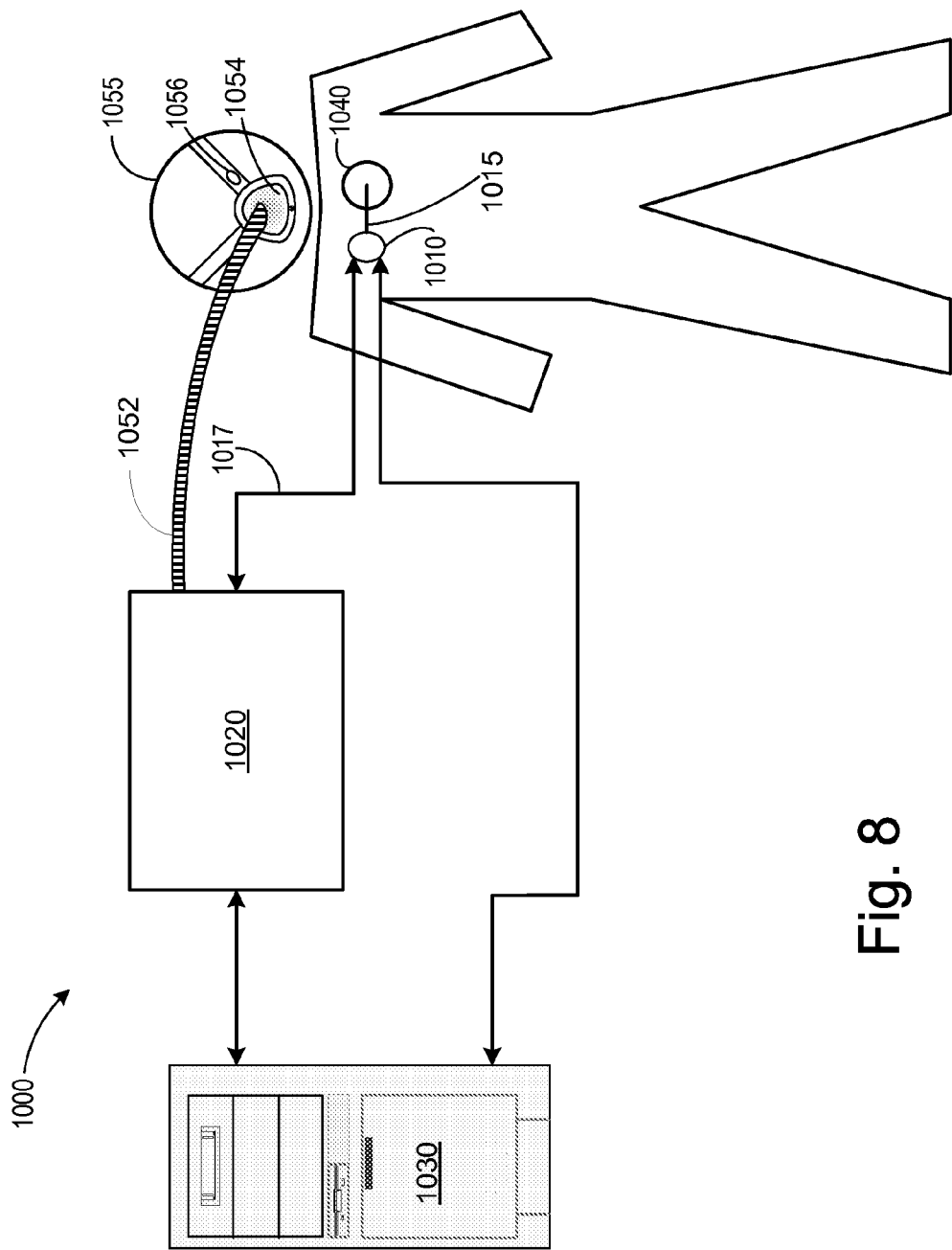
FIG. 8 illustrates a medical system including an implantable cardiac rhythm management device that cooperates with a patient-external respiration therapy device to provide coordinated patient monitoring, diagnosis and/or therapy in accordance with an embodiment of the invention.

In the example illustrated in FIG. 8, a mechanical respiration therapy device, designated CPAP device 1020, includes a positive airway pressure device that cooperates with a CRM 1010. Positive airway pressure devices may be used to provide a variety of respiration therapies, including, for example, continuous positive airway pressure (CPAP), bi-level positive airway pressure (bi-level PAP), proportional positive airway pressure (PPAP), auto-titrating positive airway pressure, ventilation, gas or oxygen therapies.

The CPAP device 1020 develops a positive air pressure that is delivered to the patient's airway through a tube system 1052 and a mask 1054 connected to the CPAP device 1020. The mask 1054 may include EMG sensors, such as an EMG sensor 1056 attached to a strap 1057 that is placed around a head 1055 of the patient. Positive airway pressure devices are often used to treat disordered breathing. In one configuration, for example, the positive airway pressure provided by the CPAP device 1020 acts as a pneumatic splint keeping the patient's airway open and reducing the severity and/or number of occurrences of disordered breathing due to airway obstruction.

The CPAP device 1020 may directly control the delivery of respiration therapy to the patient, and may contribute to the control of the CRM device 1010. In addition, the CPAP device 1020 may provide a number of monitoring and/or diagnostic functions in relation to the respiratory system and/or other physiological systems.

The CRM 1010 and CPAP 1020 devices may communicate directly through a wireless communications link 1017, for example. Alternatively, or additionally, the CRM 1010 and CPAP 1020 devices may communicate with and/or through an APM such as an APM system 1030, as will be described further below with reference to FIG. 12. The CRM 1010 may be coupled to a heart 1040 of the patient using a lead system 1015, for example.

The CRM 1010 may provide a first set of monitoring, diagnostic, and/or therapeutic functions to a patient 1055. The CRM 1010 may be electrically coupled to a patient's heart 1040 through one or more cardiac electrodes 1015 terminating in, on, or about the heart 1040. The cardiac electrodes 1015 may sense cardiac signals produced by the heart 1040 and/or provide therapy to one or more heart chambers. For example, the cardiac electrodes 1015 may deliver electrical stimulation to one or more heart 1040 chambers, and/or to one or multiple sites within the heart 1040 chambers. The CRM 1010 may directly control delivery of one or more cardiac therapies, such as cardiac pacing, defibrillation, cardioversion, cardiac resynchronization, and/or other cardiac therapies, for example. In addition, the CRM 1010 may facilitate the control of a mechanical respiration device 1020. Further, the CRM 1010 may perform various monitoring and/or diagnostic functions in relation to the cardiovascular system and/or other physiological systems.

Although FIG. 8 illustrates a CRM device 1010 used with a CPAP device 1020 to provide coordinated patient monitoring, diagnosis and/or therapy, any number of patient-internal and patient-external medical devices may be included in a medical system that detects sleep-related disorders in accordance with the invention. For example, a drug delivery device, such as a drug pump or controllable nebulizer, may be included in the system 1000. The drug delivery device may cooperate with either or both of the CRM device 1010 and the CPAP device 1020 and may contribute to the patient monitoring, diagnosis, and/or therapeutic functions of the medical system 1000.

Figure 9:
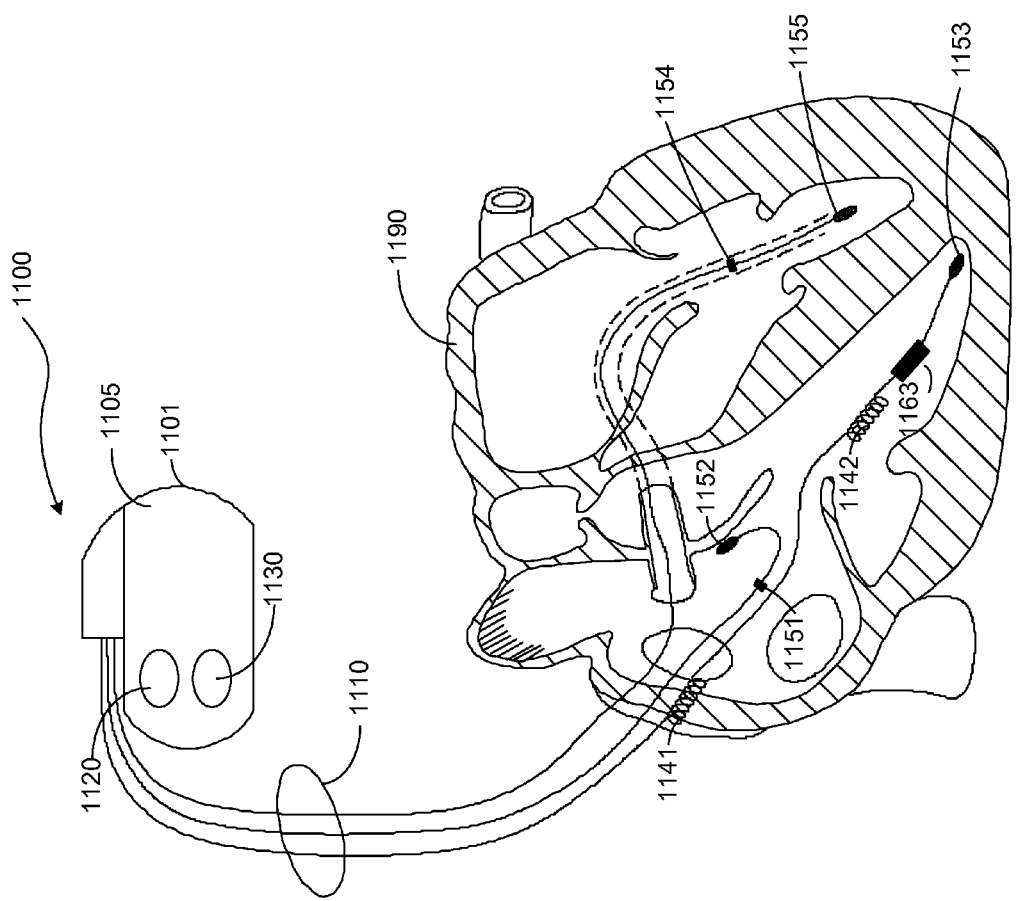
FIG. 9 is an illustration of an implantable cardiac device including a lead assembly shown implanted in a sectional view of a heart, the device used for coordinated patient monitoring, diagnosis, and/or therapy in accordance with embodiments of the invention.

Referring now to FIG. 9, the implantable device illustrated in FIG. 9 is an embodiment of a CRM 1100 including an implantable pulse generator 1105 electrically and physically coupled to an intracardiac lead system 1110.

Portions of the intracardiac lead system 1110 are inserted into the patient's heart 1190. The intracardiac lead system 1110 includes one or more electrodes configured to sense electrical cardiac activity of the heart, deliver electrical stimulation to the heart, sense the patient's transthoracic impedance, and/or sense other physiological parameters, e.g., cardiac chamber pressure or temperature. Portions of the housing 1101 of the pulse generator 1105 may optionally serve as a can electrode.

Communications circuitry is disposed within the housing 1101 for facilitating communication between the pulse generator 1105 and an external communication device, such as a portable or bedside communication station, patient-carried/worn communication station, or external programmer, for example. The communications circuitry can also facilitate unidirectional or bidirectional communication with one or more implanted, external, cutaneous, or subcutaneous physiologic or non-physiologic sensors, patient-input devices and/or information systems.

The pulse generator 1105 may optionally incorporate a motion detector 1120 that may be used to sense various respiration-related conditions. For example, the motion detector 520 may be optionally configured to sense snoring, activity level, and/or chest wall movements associated with respiratory effort, for example. The motion detector 1120 may be implemented as an accelerometer positioned in or on the housing 1101 of the pulse generator 1105. If the motion sensor is implemented as an accelerometer, the motion sensor may also provide respiratory, e.g. rales, coughing, and cardiac, e.g. S1-S4 heart sounds, murmurs, and other acoustic information.

The lead system 1110 of the CRM 1100 may incorporate one or more transthoracic impedance sensors that may be used to acquire the patient's respiration waveform, or other respiration-related information. The transthoracic impedance sensor may include, for example, one or more intracardiac electrodes 1141, 1142, 1151-1155, 1163 positioned in one or more chambers of the heart 1190. The intracardiac electrodes 1141, 1142, 1151-1155, 1163 may be coupled to impedance drive/sense circuitry 1130 positioned within the housing of the pulse generator 1105.

In one implementation, impedance drive/sense circuitry 1130 generates a current that flows through the tissue between an impedance drive electrode 1151 and a can electrode on the housing 1101 of the pulse generator 1105. The voltage at an impedance sense electrode 1152 relative to the can electrode changes as the patient's transthoracic impedance changes. The voltage signal developed between the impedance sense electrode 1152 and the can electrode is detected by the impedance sense circuitry 1130. Other locations and/or combinations of impedance sense and drive electrodes are also possible.

Figure 10:
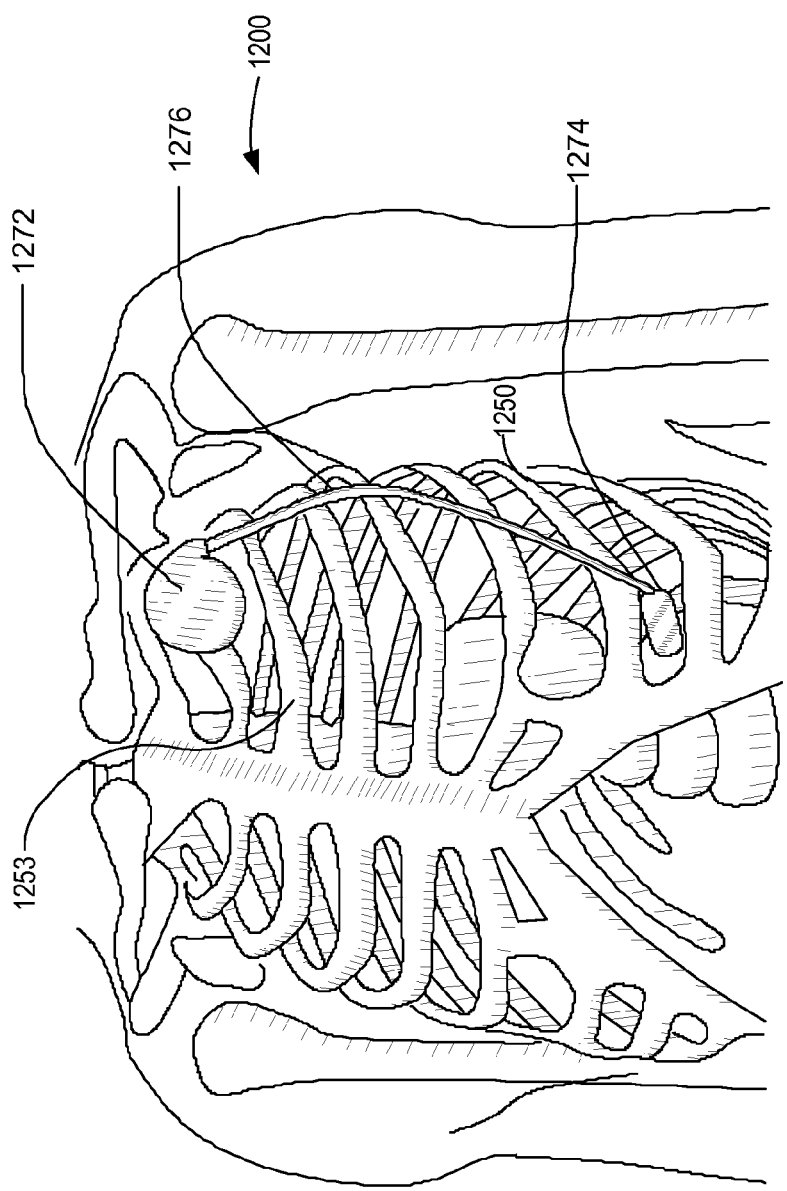
FIG. 10 is an illustration of a thorax having an implanted subcutaneous medical device that may be used for implementing diagnosis of sleep-related disorders using EMG information in accordance with an embodiment of the invention.

FIG. 10 is a diagram illustrating a subcutaneous implantable medical device 1200 that may be used for detecting EMG's and determining the presence of sleep-related muscle disorders in accordance with embodiments of the invention. The device 1200 illustrated in FIG. 10 is an ITCS device that may be implanted under the skin in the chest region of a patient. The ITCS device may, for example, be implanted subcutaneously such that all or selected elements of the device are positioned on the patient's front, back, side, or other body locations suitable for sensing cardiac activity and delivering cardiac stimulation therapy. It is understood that elements of the ITCS device may be located at several different body locations, such as in the chest, abdominal, or subclavian region with electrode elements respectively positioned at different regions near, around, in, or on the heart.

The primary housing (e.g., the active or non-active can) of the ITCS device, for example, may be configured for positioning outside of a rib cage 1250 at an intercostal or subcostal location, within the abdomen, or in the upper chest region (e.g., subclavian location, such as above a third rib 1253). In one implementation, one or more electrodes may be located on a primary housing 1272 and/or at other locations about, but not in direct contact with the heart, great vessel or coronary vasculature.

In another implementation, one or more electrodes may be located in direct contact with the heart, great vessel or coronary vasculature, such as via one or more leads implanted by use of conventional transvenous delivery approaches. In another implementation, for example, one or more subcutaneous electrode subsystems or electrode arrays may be used to sense cardiac activity and deliver cardiac stimulation energy in an ITCS device configuration employing an active can or a configuration employing a non-active can. Electrodes may be situated at anterior and/or posterior locations relative to the heart.

In particular configurations, systems and methods may perform functions traditionally performed by pacemakers, such as providing various pacing therapies as are known in the art, in addition to cardioversion/defibrillation therapies. Exemplary pacemaker circuitry, structures and functionality, aspects of which may be incorporated in an ITCS device of a type that may benefit from multi-parameter sensing configurations, are disclosed in commonly owned U.S. Pat. Nos. 4,562,841; 5,284,136; 5,376,476; 5,036,849; 5,540,727; 5,836,987; 6,044,298; and 6,055,454, which are hereby incorporated herein by reference. It is understood that ITCS device configurations may provide for non-physiologic pacing support in addition to, or to the exclusion of, bradycardia and/or anti-tachycardia pacing therapies.

An ITCS device in accordance with various embodiments may implement diagnostic and/or monitoring functions as well as provide cardiac stimulation therapy. Diagnostics functions may involve storing, trending, displaying, transmitting, and/or evaluating various indications based on the detection of EMG. Exemplary cardiac monitoring circuitry, structures and functionality, aspects of which may be incorporated in an ITCS of the invention, are disclosed in commonly owned U.S. Pat. Nos. 5,313,953; 5,388,578; and 5,411,031, which are hereby incorporated herein by reference.

An ITCS device may be used to implement various diagnostic functions, which may involve performing rate-based, pattern and rate-based, and/or morphological tachyarrhythmia discrimination analyses. Subcutaneous, cutaneous, and/or external sensors, such as those previously described, may be employed to acquire physiologic and non-physiologic information for purposes of enhancing tachyarrhythmia detection and termination. It is understood that configurations, features, and combination of features described in the present disclosure may be implemented in a wide range of implantable medical devices, and that such embodiments and features are not limited to the particular devices described herein.

In FIG. 10, there is shown a configuration of a transthoracic cardiac sensing and/or stimulation (ITCS) device having components implanted in the chest region of a patient at different locations. In the particular configuration shown in FIG. 10, the ITCS device includes the housing 1272 within which various cardiac sensing, detection, processing, and energy delivery circuitry may be housed. It is understood that the components and functionality depicted in the figures and described herein may be implemented in hardware, software, or a combination of hardware and software. It is further understood that the components and functionality depicted as separate or discrete blocks/elements in the figures in general may be implemented in combination with other components and functionality, and that the depiction of such components and functionality in individual or integral form is for purposes of clarity of explanation, and not of limitation.

Communications circuitry may be disposed within the housing 1272 for facilitating communication between the ITCS device and an external communication device, such as a portable or bedside communication station, patient-carried/worn communication station, or external programmer, for example. The communications circuitry may also facilitate unidirectional or bidirectional communication with one or more external, cutaneous, or subcutaneous physiologic or non-physiologic sensors. The housing 1272 is typically configured to include one or more electrodes (e.g., can electrode and/or indifferent electrode). Although the housing 1272 is typically configured as an active can, it is appreciated that a non-active can configuration may be implemented, in which case at least two electrodes spaced apart from the housing 1272 are employed.

In the configuration shown in FIG. 10, a subcutaneous electrode 1274 may be positioned under the skin in the chest region and situated distal from the housing 1272. The subcutaneous and, if applicable, housing electrode(s) may be positioned about the heart at various locations and orientations, such as at various anterior and/or posterior locations relative to the heart. The subcutaneous electrode 1274 is coupled to circuitry within the housing 1272 via a lead assembly 1276. One or more conductors (e.g., coils or cables) are provided within the lead assembly 1276 and electrically couple the subcutaneous electrode 1274 with circuitry in the housing 1272. One or more sense, sense/pace or defibrillation electrodes may be situated on the elongated structure of the electrode support, the housing 1272, and/or the distal electrode assembly (shown as subcutaneous electrode 1274 in the configuration shown in FIG. 10).

In one configuration, the electrode support assembly and the housing 1272 define a unitary structure (e.g., a single housing/unit). The electronic components and electrode conductors/connectors are disposed within or on the unitary ITCS device housing/electrode support assembly. At least two electrodes are supported on the unitary structure near opposing ends of the housing/electrode support assembly. The unitary structure may have an arcuate or angled shape, for example.

According to another configuration, the electrode support assembly defines a physically separable unit relative to the housing 1272. The electrode support assembly includes mechanical and electrical couplings that facilitate mating engagement with corresponding mechanical and electrical couplings of the housing 1272. For example, a header block arrangement may be configured to include both electrical and mechanical couplings that provide for mechanical and electrical connections between the electrode support assembly and housing 1272. The header block arrangement may be provided on the housing 1272 or the electrode support assembly. Alternatively, a mechanical/electrical coupler may be used to establish mechanical and electrical connections between the electrode support assembly and housing 1272. In such a configuration, a variety of different electrode support assemblies of varying shapes, sizes, and electrode configurations may be made available for physically and electrically connecting to a standard ITCS device housing 1272.

Various embodiments described herein may be used in connection with subcutaneous monitoring, diagnosis, and/or therapy. Methods, structures, and/or techniques described herein relating to subcutaneous systems and methods may incorporate features of one or more of the following references: commonly owned US Patent Applications: "Subcutaneous Cardiac Sensing, Stimulation, Lead Delivery, and Electrode Fixation Systems and Methods," Ser. No. 60/462,272, filed Apr. 11, 2003; U.S. Pat. No. 7,570,997; and U.S. Publication No. 20040215240; each hereby incorporated herein by reference.

Figure 11:
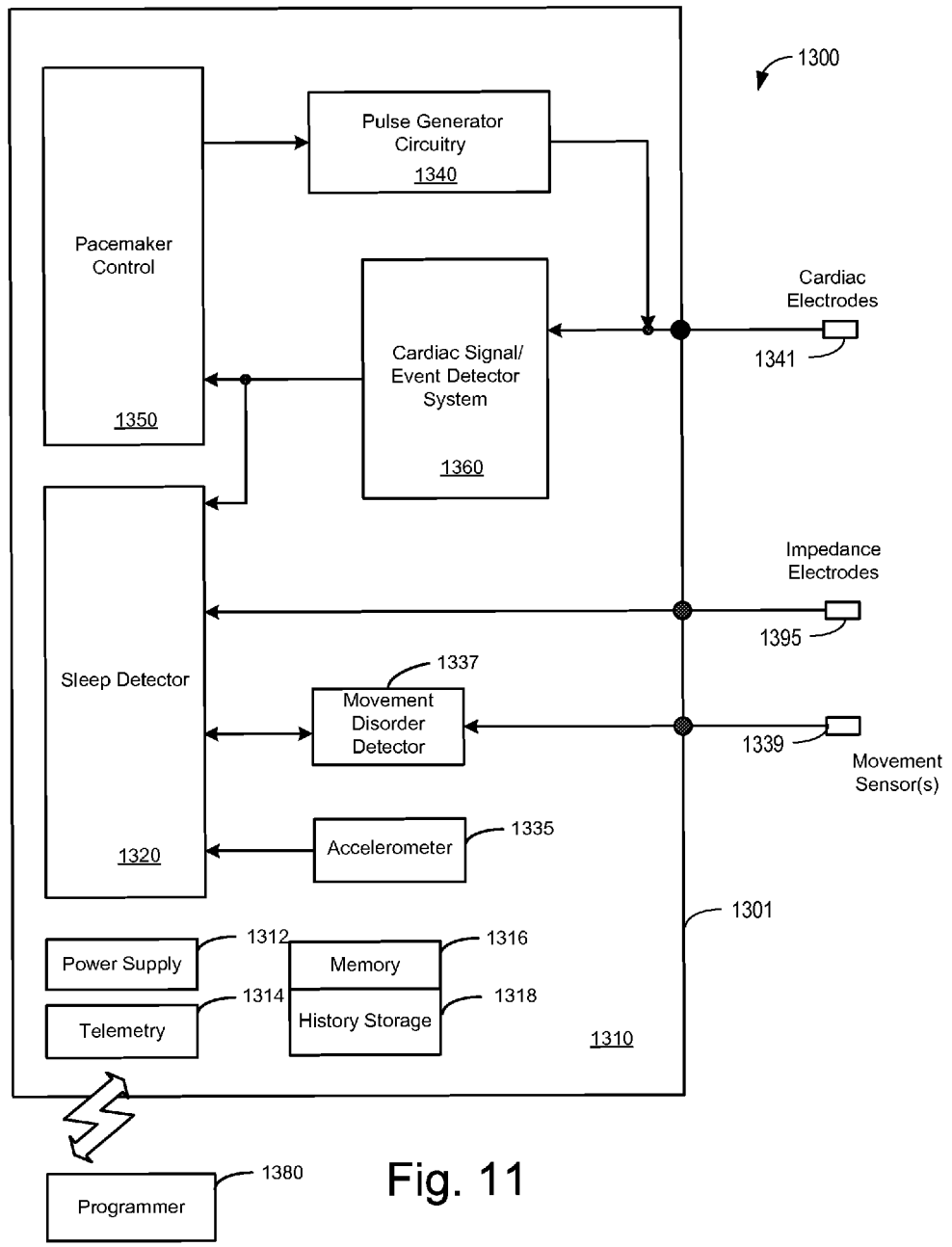
FIG. 11 is a block diagram of a cardiac rhythm management (CRM) system configured as a pacemaker and suitable for implementing diagnosis of sleep-related disorders using EMG information in accordance with embodiments of the invention.

Referring now to FIG. 11, there is shown a block diagram of an embodiment of a CRM system 1300 configured as a pacemaker and suitable for implantably detecting EMG's and determining the presence of sleep-related muscle disorders in accordance with the invention. FIG. 11 shows the CRM 1300 divided into functional blocks. The CRM 1300 includes a sleep detector 1320 for receiving sleep-related signals and detecting sleep in accordance with embodiments of the invention.

In one embodiment, the sleep detector 1320 is incorporated as part of CRM circuitry 1310 encased and hermetically sealed in a housing 1301 suitable for implanting in a human body. Power to the CRM 1300 is supplied by an electrochemical battery power supply 1312 housed within the CRM 1300. A connector block (not shown) is additionally attached to the CRM 1300 to allow for the physical and electrical attachment of the cardiac lead system conductors to the CRM circuitry 1310.

The CRM circuitry 1310 may be configured as a programmable microprocessor-based system, with circuitry for detecting sleep in addition to providing pacing therapy to the heart. Cardiac signals sensed by one or more cardiac electrodes 1341 may be processed by the cardiac event detection circuitry 1360. Pace pulses controlled by the pacemaker control 1350 and generated by the pulse generator 1340 are delivered to the heart to treat various arrhythmias of the heart.

The memory circuit 1316 may store parameters for various device operations involved in sleep detection and/or cardiac pacing and sensing. The memory circuit 1316 may also store data indicative of sleep-related signals received by components of the CRM circuitry 1310, such as information derived from one or more impedance electrodes 1395, the cardiac signal detector system 1360, the accelerometer 1335, and/or the sleep detector 1320.

As illustrated in FIG. 11, the sleep detector 1320 receives signals derived from the cardiac event detector 1360, the impedance electrodes 1395 and the accelerometer 1335 to perform operations involving detecting sleep onset and sleep termination according to the principles of the invention. Historical data storage 1318 may be coupled to the sleep detection circuitry 1320 for storing historical sleep-related data. Such data may be transmitted to an external programmer unit 1380 and used for various diagnostic purposes and as needed or desired.

Also shown in FIG. 11 is a movement disorder detector 1337 coupled to one or more movement sensors 1339. The movement disorder detector 1337 receives signals from the movement sensor(s) 1339 from which one or more movement disorders are detected, such as bruxism, periodic limb movement disorder, or restless leg syndrome. The movement sensor(s) 1339 are preferably of a type described previously. The movement disorder detector 1337 may also be coupled to the sleep detector 1320. The sleep detector 1320 may determine patient sleep status, such as sleep onset, offset, and arousal, using signals received from the movement sensor(s) 1339 and/or from the movement disorder detector 1337. The movement disorder detector 1337 may use sleep status/state information received from the sleep detector 1320 to discriminate between sleep and wakeful movement disorders.

Telemetry circuitry 1314 is coupled to the CRM circuitry 1310 to allow the CRM 1300 to communicate with a remote device such as the programmer 1380, or other device. In one embodiment, the telemetry circuitry 1314 and the programmer 1380 use a wire loop antenna and a radio frequency telemetric link to receive and transmit signals and data between the programmer 1380 and telemetry circuitry 1314. In this manner, programming commands and data may be transferred between the CRM circuitry 1310 and the one or more remote devices 1380 during and after implant.

The programming commands allow a physician to set or modify various parameters used by the CRM system 1300. These parameters may include setting sleep detection parameters for use during sleep detection, such as which sleep-related signals are to be used for sleep detection and threshold adjustment, and the initial sleep detection thresholds. In addition, the CRM system 1300 may download to the programmer 1380 stored data pertaining to sensed sleep periods, including the amount of time spent sleeping, the time of day sleep periods occurred, historical data of sleep times, and the number of arousals during the sleep periods, for example.

Still referring to FIG. 11, signals associated with patient activity may be detected through the use of an accelerometer 1335 positioned within the housing 1301 of the CRM 1300. The accelerometer 1335 may be responsive to patient activity. The accelerometer signal may be correlated with activity level or workload, for example. Signals derived from the accelerometer 1335 are coupled to the sleep detector 1320 and may also be used by the pacemaker 1350 for implementing a rate adaptive pacing regimen, for example.

The impedance electrodes 1395 sense the patient's transthoracic impedance. The transthoracic impedance may be used to calculate various parameters associated with respiration. Impedance driver circuitry (not shown) induces a current that flows through the blood between the impedance drive electrode and a can electrode on the housing 1301 of the CRM 1300. The voltage at an impedance sense electrode relative to the can electrode changes as the transthoracic impedance changes. The voltage signal developed between the impedance sense electrode and the can electrode is detected by the impedance sense amplifier and is delivered to the sleep detector circuitry 1320 for further processing.

FIG. 12 is a block diagram of a medical system 1400 that may be used to implement coordinated patient measuring and/or monitoring, diagnosis, and/or therapy, including detecting EMG's and determining the presence of sleep-related muscle disorders in accordance with embodiments of the invention. The medical system 1400 may include, for example, one or more patient-internal medical devices 1410 and one or more patient-external medical devices 1420. Each of the patient-internal 1410 and patient-external 1420 medical devices may include one or more of a patient monitoring unit 1412, 1422, a diagnostics unit 1414, 1424, and/or a therapy unit 1416, 1426.

The patient-internal medical device 1410 is typically a fully or partially implantable device that performs measuring, monitoring, diagnosis, and/or therapy functions. The patient-external medical device 1420 performs monitoring, diagnosis and/or therapy functions external to the patient (i.e., not invasively implanted within the patient's body). The patient-external medical device 1420 may be positioned on the patient, near the patient, or in any location external to the patient. It is understood that a portion of a patient-external medical device 1420 may be positioned within an orifice of the body, such as the nasal cavity or mouth, yet may be considered external to the patient (e.g., mouth pieces/appliances, tubes/appliances for nostrils, or temperature sensors positioned in the ear canal).

The patient-internal and patient-external medical devices 1410, 1420 may be coupled to one or more sensors 1441, 1442, 1445, 1446, patient input devices 1443, 1447 and/or other information acquisition devices 1444, 1448. The sensors 1441, 1442, 1445, 1446, patient input devices 1443, 1447, and/or other information acquisition devices 1444, 1448 may be employed to detect conditions relevant to the monitoring, diagnostic, and/or therapeutic functions of the patient-internal and patient-external medical devices 1410, 1420.

The medical devices 1410, 1420 may each be coupled to one or more patient-internal sensors 1441, 1445 that are fully or partially implantable within the patient. The medical devices 1410, 1420 may also be coupled to patient-external sensors positioned on, near, or in a remote location with respect to the patient. The patient-internal and patient-external sensors are used to sense conditions, such as physiological or environmental conditions, that affect the patient.

The patient-internal sensors 1441 may be coupled to the patient-internal medical device 1410 through one or more internal leads 1453. In one example, as was described above with reference to FIG. 9, an internal endocardial lead system is used to couple cardiac electrodes to an implantable pacemaker or other cardiac rhythm management device. Still referring to FIG. 12, one or more patient-internal sensors 1441 may be equipped with transceiver circuitry to support wireless communications between the one or more patient-internal sensors 1441 and the patient-internal medical device 1410 and/or the patient-external medical device 1420. The patient-external sensors 1442 may be coupled to the patient-internal medical device 1410 and/or the patient-external medical device 1420 through one or more internal leads 1455 or through wireless connections. Patient-external sensors 1442 may communicate with the patient-internal medical device 1410 wirelessly. Patient-external sensors 1446 may be coupled to the patient-external medical device 1420 through one or more internal leads 1457 or through a wireless link.

The medical devices 1410, 1420 may be coupled to one or more patient input devices 1443, 1447. The patient input devices are used to allow the patient to manually transfer information to the medical devices 1410, 1420. The patient input devices 1443, 1447 may be particularly useful for inputting information concerning patient perceptions, such as how well the patient feels, and information such as patient smoking, drug use, or other activities that are not automatically sensed or detected by the medical devices 1410, 1420.

One or more of sensors 1440, 1442, 1445, 1446 may be configured to detect conditions associated with sleep-related muscle disorders. For example, one or more of sensors 1440, 1442, 1445, 1446 may be implemented as an EMG sensor, and one or more of sensors 1440, 1442, 1445, 1446 may be implemented as a respiration sensor. The EMG and respiration sensors may be coupled to diagnostics unit 1414, 1424 for detection of sleep-related muscle disorders.

The medical devices 1410, 1420 may be connected to one or more information acquisition devices 1444, 1448, for example, a database that stores information useful in connection with the monitoring, diagnostic, or therapy functions of the medical devices 1410, 1420. For example, one or more of the medical devices 1410, 1420 may be coupled through a network to a patient information server 1430 that provides information about environmental conditions affecting the patient, e.g., the pollution index for the patient's location.

In one embodiment, the patient-internal medical device 1410 and the patient-external medical device 1420 may communicate through a wireless link between the medical devices 1410, 1420. For example, the patient-internal and patient-external devices 1410, 1420 may be coupled through a short-range radio link, such as Bluetooth, IEEE 802.11, and/or a proprietary wireless protocol. The communications link may facilitate uni-directional or bi-directional communication between the patient-internal 1410 and patient-external 1420 medical devices. Data and/or control signals may be transmitted between the patient-internal 1410 and patient-external 1420 medical devices to coordinate the functions of the medical devices 1410, 1420.

In another embodiment, the patient-internal and patient-external medical devices 1410, 1420 may be used within the structure of an advanced patient management system (APM) 1440. Advanced patient management systems 1440 involve a system of medical devices that are accessible through various communications technologies. For example, patient data may be downloaded from one or more of the medical devices periodically or on command, and stored at the patient information server 1430. The physician and/or the patient may communicate with the medical devices and the patient information server 1430, for example, to acquire patient data or to initiate, terminate or modify therapy.

The data stored on the patient information server 1430 may be accessible by the patient and the patient's physician through one or more terminals 1450, e.g., remote computers located in the patient's home or the physician's office. The patient information server 1430 may be used to communicate to one or more of the patient-internal and patient-external medical devices 1410, 1420 to provide remote control of the monitoring, diagnosis, and/or therapy functions of the medical devices 1410, 1420.

In one embodiment, the patient's physician may access patient data transmitted from the medical devices 1410, 1420 to the patient information server 1430. After evaluation of the patient data, the patient's physician may communicate with one or more of the patient-internal or patient-external devices 1410, 1420 through the APM system 1440 to initiate, terminate, or modify the monitoring, diagnostic, and/or therapy functions of the patient-internal and/or patient-external medical systems 1410, 1420. Systems and methods involving advanced patient management techniques are further described in U.S. Pat. Nos. 6,336,903, 6,312,378, 6,270,457, and 6,398,728, hereby incorporated herein by reference.

In another embodiment, the patient-internal and patient-external medical devices 1410, 1420 may not communicate directly, but may communicate indirectly through the APM system 1440. In this embodiment, the APM system 1440 may operate as an intermediary between two or more of the medical devices 1410, 1420. For example, data and/or control information may be transferred from one of the medical devices 1410, 1420 to the APM system 1440. The APM system 1440 may transfer the data and/or control information to another of the medical devices 1410, 1420.

In one embodiment, the APM system 1440 may communicate directly with the patient-internal and/or patient-external medical devices 1410, 1420. In another embodiment, the APM system 1440 may communicate with the patient-internal and/or patient-external medical devices 1410, 1420 through medical device programmers 1460, 1470 respectively associated with each medical device 1410, 1420.

Various embodiments described herein may be used in connection with advanced patient management. Methods, structures, and/or techniques described herein relating to advanced patient management, such as those involving remote patient/device monitoring, diagnosis, therapy, or other advanced patient management related methodologies, may incorporate features of one or more of the following references: U.S. Pat. Nos. 6,221,011; 6,277,072; 6,280,380; 6,358,203; 6,368,284; and 6,440,066 each hereby incorporated herein by reference.

According to one embodiment of the invention, illustrated in FIG. 8, a medical system 1000 may include an implantable cardiac rhythm management device 1010 that cooperates with a patient-external respiration therapy device 1020 to provide coordinated patient monitoring, diagnosis and/or therapy. In this configuration, the implantable cardiac rhythm management device (CRM) 1010 operates as the patient-internal medical device 1410 described with reference to FIG. 12.

The following commonly owned U.S. Pat. Nos. 7,189,204; 7,252,640; 7,396,333, 7,680,537; and 7,720,541 are hereby incorporated by reference. Features and aspects of these applications may be incorporated within the context of systems, devices, methods, and processes implemented in accordance with embodiments of the present invention.

A number of the examples presented herein involve block diagrams illustrating functional blocks used for coordinated monitoring, diagnosis and/or therapy functions in accordance with embodiments of the invention. It will be understood by those skilled in the art that there exist many possible configurations in which these functional blocks may be arranged and implemented. The examples depicted herein provide examples of possible functional arrangements used to implement the approaches of the invention.

Each feature disclosed in this specification (including any accompanying claims, abstract, and drawings), may be replaced by alternative features having the same, equivalent or similar purpose, unless expressly stated otherwise. Thus, unless expressly stated otherwise, each feature disclosed is one example only of a generic series of equivalent or similar features.

Various modifications and additions can be made to the embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A system, comprising:
a plurality of sensors configured to respectively sense a plurality of physiological signals including at least muscle movement signals comprising electromyogram signals;
a detector configured to detect sleep-related disorder events using the sensed physiological signals, the sleep-related disorder events comprising involuntary muscle movement events of non-respiratory muscles and sleep-disordered breathing events, the detection of the sleep-disordered breathing events and the involuntary muscle movement events based at least in part on the electromyogram signals; and
a processor configured to calculate a composite sleep disorder index, the composite sleep disorder index quantifying combined effect of the involuntary muscle movement events and the sleep-disordered breathing events, wherein at least one of calculating and detecting is configured to be implemented at least in part patient-internally.

2. The system of claim 1, further comprising communications circuitry configured to communicate one or both of the plurality of physiological signals and information associated with the detected sleep-related disorder events to a patient-external processing system.

3. The system of claim 1, further comprising communications circuitry configured to communicate one or more of the plurality of physiological signals, information associated with the detected sleep-related disorder events, and the composite sleep disorder index to an implantable medical device.

4. The system of claim 1, further comprising at least one of a controller configured to control therapy to treat a condition associated with one or more of the detected sleep-related disorder events based on the sleep movement disorder index and a therapy delivery unit configured to deliver the therapy to treat the condition associated with one or more of the detected sleep-related disorder events based on the composite sleep disorder index.

5. The system of claim 1, wherein the processor is configured to calculate the composite sleep disorder index including calculating an apnea/hypopnea index and a movement disorder index, the apnea/hypopnea index representative of an amount of apnea and hypopnea events relative to time and the movement disorder index representative of an amount of the involuntary muscle movement events relative to time.

6. The system of claim 1, wherein the sleep-disordered breathing events comprise one or more of sleep apnea, hypopnea, and Cheyne-Stokes respiration.

7. The system of claim 1, wherein the involuntary muscle movement events comprise one or more of bruxism, periodic limb movement disorder, and restless leg syndrome.

8. The system of claim 1, wherein the plurality of sensors includes a transthoracic impendence sensor.

9. The system of claim 1, wherein the processor is further configured to determine one or more sleep stages based at least in part on one or more of the physiological signals.

10. The system of claim 1, wherein the processor is further configured to determine a patient's arousal from sleep events.

11. The system of claim 1, further comprising an implantable device configured to deliver a therapy in response to the composite sleep disorder index.

12. The system of claim 1, further comprising a positive airway pressure device configured to deliver a respiratory therapy in response to the composite sleep disorder index.

13. The system of claim 1, further comprising a drug delivery device configured to treat the involuntary muscle movement events.

14. The system of claim 1, further comprising a transcutaneous electric nerve stimulation therapy device configured to treat the involuntary muscle movement events.

15. A system, comprising:
a plurality of sensors configured to respectively sense a plurality of physiological signals including at least one muscle movement signal;
one or more electrical components structured to:
detect sleep-related disorder events using the sensed physiological signals, the sleep-related disorder events including involuntary muscle movement events of non-respiratory muscles and sleep-disordered breathing events; and
determine a composite sleep disorder index, the composite sleep disorder index quantifying combined effect of the involuntary muscle movement events and the sleep-disordered breathing events.

16. The system of claim 15, wherein the one or more electrical components includes two or more electrical components, with at least one of the two or more electrical components is configured to be implanted patient-internally.

17. The system of claim 16, wherein at least one of the two or more electrical components is part of a patient-external processing system.

18. The system of claim 15, wherein the sleep-disordered breathing events include one or more of sleep apnea, hypopnea, and Cheyne-Stokes respiration.

19. The system of claim 15, wherein the involuntary muscle movement events include one or more of bruxism, periodic limb movement disorder, and restless leg syndrome.

20. A system, comprising:
a plurality of sensors configured to respectively sense a plurality of physiological signals including at least one muscle movement signal that is an electromyogram signal;
one or more electrical components structured to:
detect sleep-related disorder events using the sensed physiological signals, the sleep-related disorder events including involuntary muscle movement events of non-respiratory muscles and sleep-disordered breathing events, the detection of the sleep-disordered breathing events and/or the involuntary muscle movement events based at least in part on the electromyogram signal; and
determine a composite sleep disorder index, the composite sleep disorder index quantifying combined effect of the involuntary muscle movement events and the sleep-disordered breathing events, wherein at least one of determining and detecting is configured to be implemented at least in part patient-internally.

* * * * *